US009977232B2

(12) United States Patent
Otani

(10) Patent No.: US 9,977,232 B2
(45) Date of Patent: May 22, 2018

(54) LIGHT SOURCE DEVICE FOR ENDOSCOPE, ENDOSCOPE SYSTEM, AND METHOD FOR OPERATING LIGHT SOURCE DEVICE FOR ENDOSCOPE

(71) Applicant: FUJIFILM Corporation, Tokyo (JP)

(72) Inventor: Kenichi Otani, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 146 days.

(21) Appl. No.: 15/009,659

(22) Filed: Jan. 28, 2016

(65) Prior Publication Data

US 2016/0223807 A1 Aug. 4, 2016

(30) Foreign Application Priority Data

Jan. 29, 2015 (JP) .................................. 2015-015178
Jul. 30, 2015 (JP) .................................. 2015-150941

(51) Int. Cl.
*F21V 9/00* (2018.01)
*G02B 23/24* (2006.01)
(Continued)

(52) U.S. Cl.
CPC ........ *G02B 23/2461* (2013.01); *A61B 1/0638* (2013.01); *G02B 27/1006* (2013.01)

(58) Field of Classification Search
CPC ... A61B 1/0638; A61B 1/0661; A61B 1/0684; F21Y 2113/00; F21Y 2113/10; G02B 23/2461; G02B 27/1006
See application file for complete search history.

(56) References Cited

U.S. PATENT DOCUMENTS 9,029,755 B2 * 5/2015 Ono ....................... G02B 26/02
250/208.1
9,066,677 B2 * 6/2015 Seto ..................... A61B 1/0638
(Continued)

FOREIGN PATENT DOCUMENTS

JP 2011-10998 A 1/2011
JP 2011-36361 A 2/2011
(Continued)

OTHER PUBLICATIONS

Japanese Notification of Reasons for Refusal for corresponding Japanese Application No. 2015-150941, dated Feb. 2, 2018, with Machine translation.

*Primary Examiner* — Thien M Le
*Assistant Examiner* — April Taylor
(74) *Attorney, Agent, or Firm* — Birch, Stewart, Kolasch & Birch, LLP

(57) ABSTRACT

A light source device for an endoscope comprises a light source unit and a light source controller. The light source unit has LEDs independently emitting light of respective different colors, and emits first multicolor spectrum light having a first multicolor spectrum, into which the light from the LEDs is combined. The light source controller makes a light quantity integral of the first multicolor spectrum light in a first wavelength band equal to a light quantity integral of continuous-spectrum light in the first wavelength band and makes a light quantity integral of the first multicolor spectrum light in a second wavelength band equal to a light quantity integral of the continuous-spectrum light in the second wavelength band. The continuous-spectrum light includes at least a part of a wavelength band of light emitted from a white light source. The second wavelength band is different from the first wavelength band.

17 Claims, 13 Drawing Sheets

(51) Int. Cl.
*G02B 27/10* (2006.01)
*A61B 1/06* (2006.01)

(56) References Cited

U.S. PATENT DOCUMENTS

| | | |
|---|---|---|
| 2011/0034770 A1 | 2/2011 | Endo et al. |
| 2012/0116157 A1* | 5/2012 | Seto .................. A61B 1/00057 600/109 |
| 2012/0116159 A1 | 5/2012 | Mizuyoshi et al. |
| 2015/0092035 A1 | 4/2015 | Yamamoto et al. |
| 2016/0037999 A1 | 2/2016 | Yabe et al. |
| 2016/0360125 A1* | 12/2016 | Yamamoto ............... A61B 1/06 |
| 2017/0264078 A1* | 9/2017 | Daidoji ................. H01S 5/0617 |

FOREIGN PATENT DOCUMENTS

| | | |
|---|---|---|
| JP | 2011-201697 A | 10/2011 |
| JP | 2013-111177 A | 6/2013 |
| JP | 2013-202166 A | 10/2013 |
| JP | 2013-255655 A | 12/2013 |
| WO | WO 2015/005277 A1 | 1/2015 |

* cited by examiner

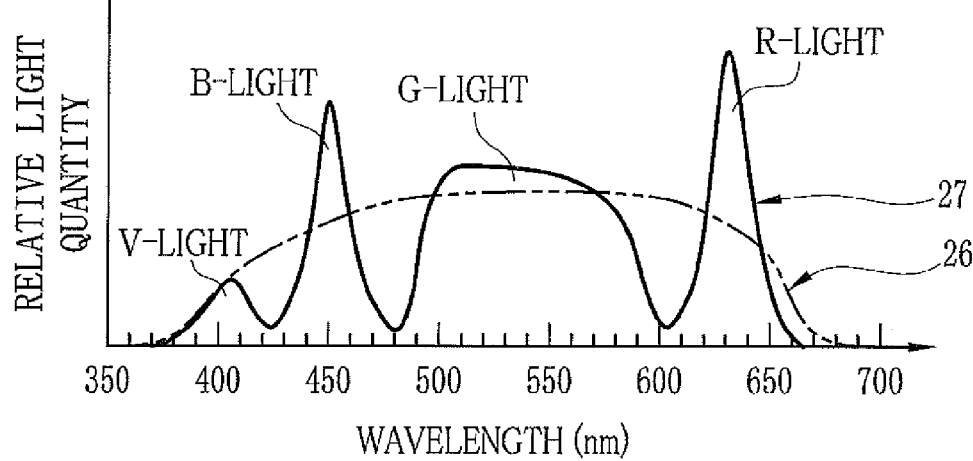
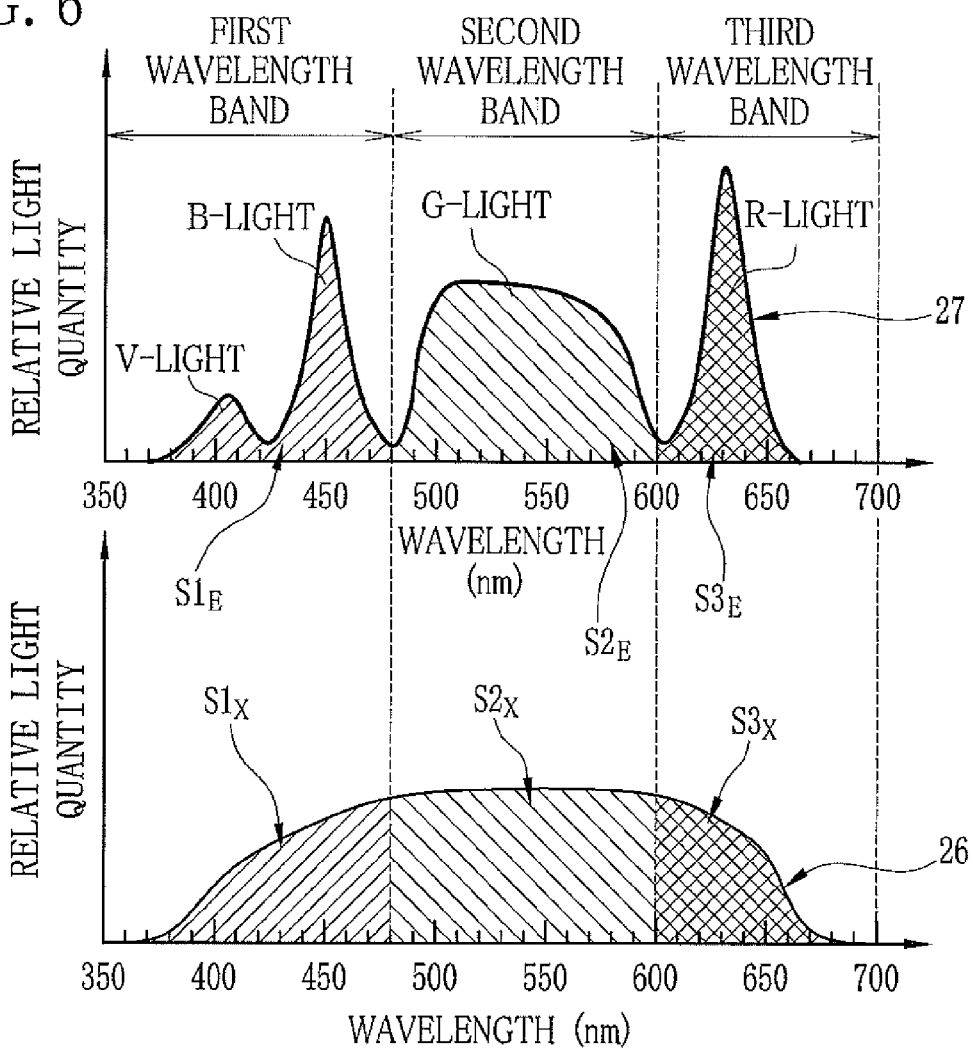

LIGHT SOURCE DEVICE FOR ENDOSCOPE, ENDOSCOPE SYSTEM, AND METHOD FOR OPERATING LIGHT SOURCE DEVICE FOR ENDOSCOPE

CROSS-REFERENCE TO RELATED APPLICATIONS

The present application claims priority under 35 U.S.C. § 119 to Japanese Patent Application No. 2015-015178, filed Jan. 29, 2015 and Japanese Patent Application No. 2015-150941, filed Jul. 30, 2015. Each of the above applications is hereby expressly incorporated by reference, in its entirety, into the present application.

BACKGROUND OF THE INVENTION

1. Field of the Invention

The present invention relates to a light source device for endoscope that applies illumination light that is combination of light from two or more light sources to an object of interest, an endoscope system, and a method for operating a light source device for endoscope.

2. Description Related to the Prior Art

Diagnoses using endoscope systems are widely performed in medical fields. The endoscope system comprises a light source device for an endoscope, an endoscope, and a processor device. The light source device generates illumination light applied to an object of interest (e.g. mucosa) in a body cavity. A light source (e.g. a xenon lamp) that emits light (hereinafter referred to as the continuous-spectrum light) having a broad continuous spectrum has been used as the light source device. Recently, however, a semiconductor light source (e.g. an LED (light emitting diode) or the like) has been replacing the broadband light source (e.g. the xenon lamp). In the case where the semiconductor light sources are used as the light sources, for example, two or more types of semiconductor light sources (e.g. a blue LED, a green LED, and a red LED) that emit light beams of different colors are used in combination. Thereby the light beams (hereinafter referred to as the multicolor spectrum light) having an optical spectrum (hereinafter may simply referred to as the spectrum) into which the spectrums of the light beams of different colors are combined are used as the illumination light.

For example, a light source device for an endoscope in an endoscope system described in US2015/0092035 (corresponding to Japanese Patent Laid-Open Publication No. 2013-255655) has four semiconductor light sources controlled independently. A spectrum, in which the light quantity distribution varies at each wavelength, of the illumination light is adjusted by controlling a light emission quantity (the light quantity) of each semiconductor light source. Thereby the object is irradiated with the illumination light having the properties suitable for the properties of an image to be captured. To be more specific, the spectrum of the illumination light is adjusted to capture, for example, an image with wide dynamic range of brightness, an image with low color temperature, an image with high color temperature, an image under the illumination of special narrowband light applied to a small area, or the like.

An endoscope system described in Japanese Patent Laid-Open Publication No. 2013-202166 has two or more semiconductor light sources controlled independently. The endoscope system identifies the model of the endoscope used and sets the conditions for driving each semiconductor light source in accordance with the model of the endoscope. To be more specific, the model of the endoscope is identified to set the light quantity ratio among the semiconductor light sources in accordance with the light transmission characteristics of a light guide, which transmits the illumination light, because the light transmission characteristics of the light guide varies according to the model.

As described above, with regard to the illumination light used in the endoscope system, the multicolor spectrum light of the semiconductor light sources is on its way to replace the continuous-spectrum light of the conventional xenon lamp or the like. The continuous-spectrum light is different from the multicolor spectrum light in spectrum. An image of an object captured under the illumination of the continuous-spectrum light may look different from an image of the object captured under the illumination of the multicolor spectrum light. Which one of the image captured under the illumination of the continuous-spectrum light and the image captured under the illumination of the multicolor spectrum light is suitable depends on circumstances. However, the adjustment of the multicolor spectrum light is easier than that of the continuous-spectrum light because the semiconductor light sources are controlled independently to make the spectrum of the illumination light suitable for the object.

For a long time, many doctors have been using the endoscope system utilizing the continuous-spectrum light of the xenon lamp or the like as the illumination light. Such doctors are accustomed to the images of an object captured under the illumination of the continuous-spectrum light. For this reason, it is necessary that the images captured under the illumination of the multicolor spectrum light of the semiconductor light sources can be observed in a comparable manner to those captured under the illumination of the continuous-spectrum light (in other words, it is necessary that the images captured under the illumination of the multicolor spectrum light are able to be compared with those captured under the illumination of the continuous-spectrum light). Many endoscopic images stored in past cases were captured under the illumination of the continuous-spectrum light. It is necessary to make the endoscopic image captured under the illumination of the multicolor spectrum light comparable to the endoscopic image captured under the illumination of the broadband continuous-spectrum light, to compare them easily.

To meet the above-described necessities, the spectrum of the broadband continuous-spectrum light may be reproduced using the semiconductor light sources. Actually, however, it is impossible for the semiconductor light sources to completely reproduce the spectrum of the broadband continuous-spectrum light. For example, in the case where the light sources are a blue LED and a green LED and a light quantity of each of the LEDs decreases as the difference between the center wavelength and the wavelength of the illumination light increases, it is difficult to change the light quantity of the light of the color between blue and green (the light in a wavelength range located at about the midpoint between the blue and green wavelengths) only by adjusting the light quantities of the blue and green LEDs. In the case where the light quantity of the light at the center wavelength emitted from each of the blue and green LEDs is made close to the light quantity of the broadband continuous-spectrum light, the light quantity of the light of the color between blue and green is substantially less than that of the broadband continuous-spectrum light. In the case where the light quantities of the blue LED and the green LED are increased to make the light quantity of the light of the color between green and blue close to that of the broadband continuous-spectrum light, each of the light quantity of the light at around the center wavelength of the blue LED and the light quantity of the light at around the center wavelength of the green LED significantly exceeds the light quantity of the broadband continuous-spectrum light.

SUMMARY OF THE INVENTION

An object of the present invention is to provide a light source device for an endoscope, an endoscope system, and a method for operating a light source device for endoscope that enable observation of an object of interest under illumination of multicolor spectrum light, into which light of different colors emitted from two or more light sources independently emitting the light of the different colors are combined, in a comparable manner to observation of the object of interest under illumination of broadband continuous-spectrum light.

An aspect of the present invention provides a light source device comprising a light source unit and a light source controller. The light source unit has two or more light sources. The light sources independently emit light of different colors. The light from the light sources is combined into first multicolor spectrum light having a first multicolor spectrum. The light source unit emits the first multicolor spectrum light. The light source controller is configured to control the light sources. The light source controller makes a light quantity integral of the first multicolor spectrum light in a first wavelength band equal to a light quantity integral of continuous-spectrum light in the first length band and makes a light quantity integral of the first multicolor spectrum light in a second wavelength band equal to a light quantity integral of the continuous-spectrum light in the second wavelength band. The continuous-spectrum light includes at least a part of a wavelength band of light emitted from a white light source. The second wavelength band is different from the first wavelength band.

It is preferred that the continuous-spectrum light is white light.

It is preferred that the white light is emitted from a xenon lamp.

It is preferred that the first wavelength band is a wavelength range including a violet wavelength range and a blue wavelength range. It is preferred that the second wavelength band is a green wavelength range.

It is preferred that the light sources include a violet light source emitting violet light and a blue light source emitting blue light. It is preferred that the first wavelength band of the first multicolor spectrum light is a wavelength range including the violet light and the blue light.

It is preferred that the light source controller further makes a light quantity integral of the first multicolor spectrum light in a third wavelength band equal to a light quantity integral of the continuous-spectrum light in the third wavelength band, the third wavelength band being different from each of the first wavelength band and the second wavelength band.

It is preferred that the third wavelength band is a red wavelength range.

It is preferred that the light source unit emits second multicolor spectrum light having a second multicolor spectrum through the light sources. The second multicolor spectrum is different from the first multicolor spectrum of the first multicolor spectrum light and different from a spectrum of the continuous-spectrum light. It is preferred that the light source controller makes a light quantity integral of the second multicolor spectrum light in the first wavelength band greater than the light quantity integral of the continuous-spectrum light in the first wavelength band and makes a light quantity integral of the second multicolor spectrum light in the second wavelength band equal to the light quantity integral of the continuous-spectrum light in the second wavelength band.

It is preferred that the light source device further comprises a light quantity detector for detecting a light quantity of the light from each of the light sources. It is preferred that, based on a light quantity of the light source with the largest shortage of the light quantity among the light sources relative to a specified light quantity for generating the first multicolor spectrum light, the light source controller sets light quantities of the rest of the light sources with the use of a result of the detection detected by the light quantity detector.

It is preferred that the light quantity detector repeats the detection of the light quantity of the light from each of the light sources while the light sources emit the light.

It is preferred that the light source device further comprises a verifier. The verifier verifies whether the light quantity integral of the first multicolor spectrum light in the first wavelength band equals the light quantity integral of the continuous-spectrum light in the first wavelength band and whether the light quantity integral of the first multicolor spectrum light in the second wavelength band equals the light quantity integral of the continuous-spectrum light in the second wavelength band.

It is preferred that the light source controller uses a result of the verification verified by the verifier, to control the light sources.

An aspect of the present invention provides an endoscope system comprising a light source unit and a light source controller. The light source unit has two or more light sources. The light sources independently emit light of different colors. The light from the light sources is combined into first multicolor spectrum light having a first multicolor spectrum. The light source unit emits the first multicolor spectrum light. The light source controller is configured to control the light sources. The light source controller makes a light quantity integral of the first multicolor spectrum light in a first wavelength band equal to a light quantity integral of continuous-spectrum light in the first length band and makes a light quantity integral of the first multicolor spectrum light in a second wavelength band equal to a light quantity integral of the continuous-spectrum light in the second wavelength band. The continuous-spectrum light includes at least a part of a wavelength band of light emitted from a white light source. The second wavelength band is different from the first wavelength band.

It is preferred that the light source unit emits second multicolor spectrum light having a second multicolor spectrum through the light sources. The second multicolor spectrum is different from the first multicolor spectrum of the first multicolor spectrum light and different from a spectrum of the continuous-spectrum light. It is preferred that the light source controller makes a light quantity integral of the second multicolor spectrum light in the first wavelength band greater than the light quantity integral of the continuous-spectrum light in the first wavelength band and makes a light quantity integral of the second multicolor spectrum light in the second wavelength band equal to the light quantity integral of the continuous-spectrum light in the second wavelength band.

It is preferred that the endoscope system further comprises a model detector. The model detector detects a model of an endoscope connected and inputs a result of the detection to the light source controller. It is preferred that the light source controller selects the light emitted from the light source unit between the first multicolor spectrum light and the second multicolor spectrum light in accordance with the model of the endoscope detected by the model detector.

It is preferred that the light source controller allows the light source unit to emit the first multicolor spectrum light in a case where the endoscope is of a model using the continuous-spectrum light and allows the light source unit to emit the second multicolor spectrum light in a case where the endoscope is of a model not using the continuous-spectrum light.

An aspect of the present invention provides a method for operating a light source device for an endoscope, comprising a preparation step and a control step. The light source device comprises a light source unit having two or more light sources. The light sources independently emit light of different colors. The light from the light sources is combined into first multicolor spectrum light having a first multicolor spectrum. The light source unit emits the first multicolor spectrum light. In the preparation step, the light source is prepared. In the control step, a light source controller controls the light sources. The light source controller makes a light quantity integral of the first multicolor spectrum light in a first wavelength band equal to a light quantity integral of continuous-spectrum light in the first length band and makes a light quantity integral of the first multicolor spectrum light in a second wavelength band equal to a light quantity integral of the continuous-spectrum light in the second wavelength band. The continuous-spectrum light includes at least a part of a wavelength band of light emitted from a white light source. The second wavelength band is different from the first wavelength band.

According to the aspects of the present invention, the light source device, the endoscope system, and the method for operating the light source device makes the light quantity integral of the multicolor spectrum light equal to the light quantity integral of the broadband continuous-spectrum light in at least two wavelength bands. Thereby the light source device, the endoscope system, and the method for operating a light source device enable observation of an object of interest under illumination of multicolor spectrum light in a comparable manner to observation of the object of interest under illumination of broadband continuous-spectrum light.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 5 is a graph illustrating a spectrum of first multicolor spectrum light;

FIG. 6 is an explanatory view illustrating a relationship between first multicolor spectrum light and continuous-spectrum light from the xenon lamp;

DESCRIPTION OF THE PREFERRED EMBODIMENTS

First Embodiment

Figure 1:
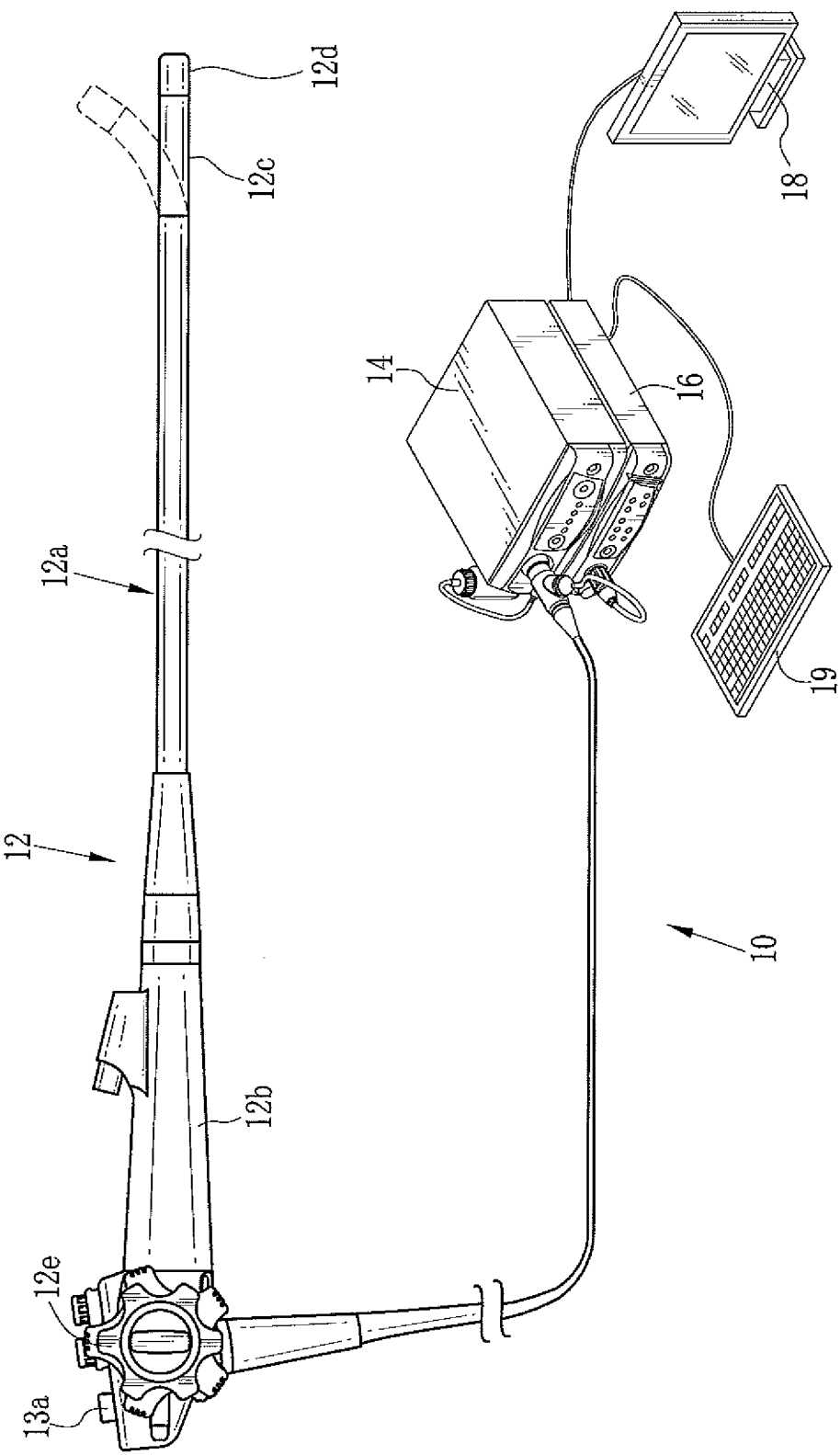
FIG. 1 is an external view of an endoscope system.

In FIG. 1, an endoscope system 10 comprises an endoscope 12, a light source device 14 for endoscope (hereinafter simply referred to as the light source device 14), a processor device 16, a monitor 18, and a console 19. The endoscope 12 is connected optically to the light source device 14 and electrically to the processor device 16. The endoscope 12 comprises an insertion section 12a to be inserted into a body cavity, a control handle unit 12b provided at the proximal end of the insertion section 12a, a flexible portion 12c, and a distal portion 12d. The distal portion 12d is coupled to the flexible portion 12c, which is provided on the distal side of the insertion section 12a. The flexible portion 12c is bent by operating an angle knob 12e of the control handle unit 12b. Thereby the distal portion 12d is directed to a desired direction. The control handle unit 12b is also provided with a zoom operating section 13 and the like.

The processor device 16 is electrically connected to the monitor 18 and the console 19. The monitor 18 outputs image(s) in each observation mode, image information associated with the corresponding image, and the like. The console 19 functions as a UI (user interface), which receives input operation such as setting a function. Note that an external storage unit (not shown) for recording the images and the image information may be connected to the processor device 16.

Figure 2:
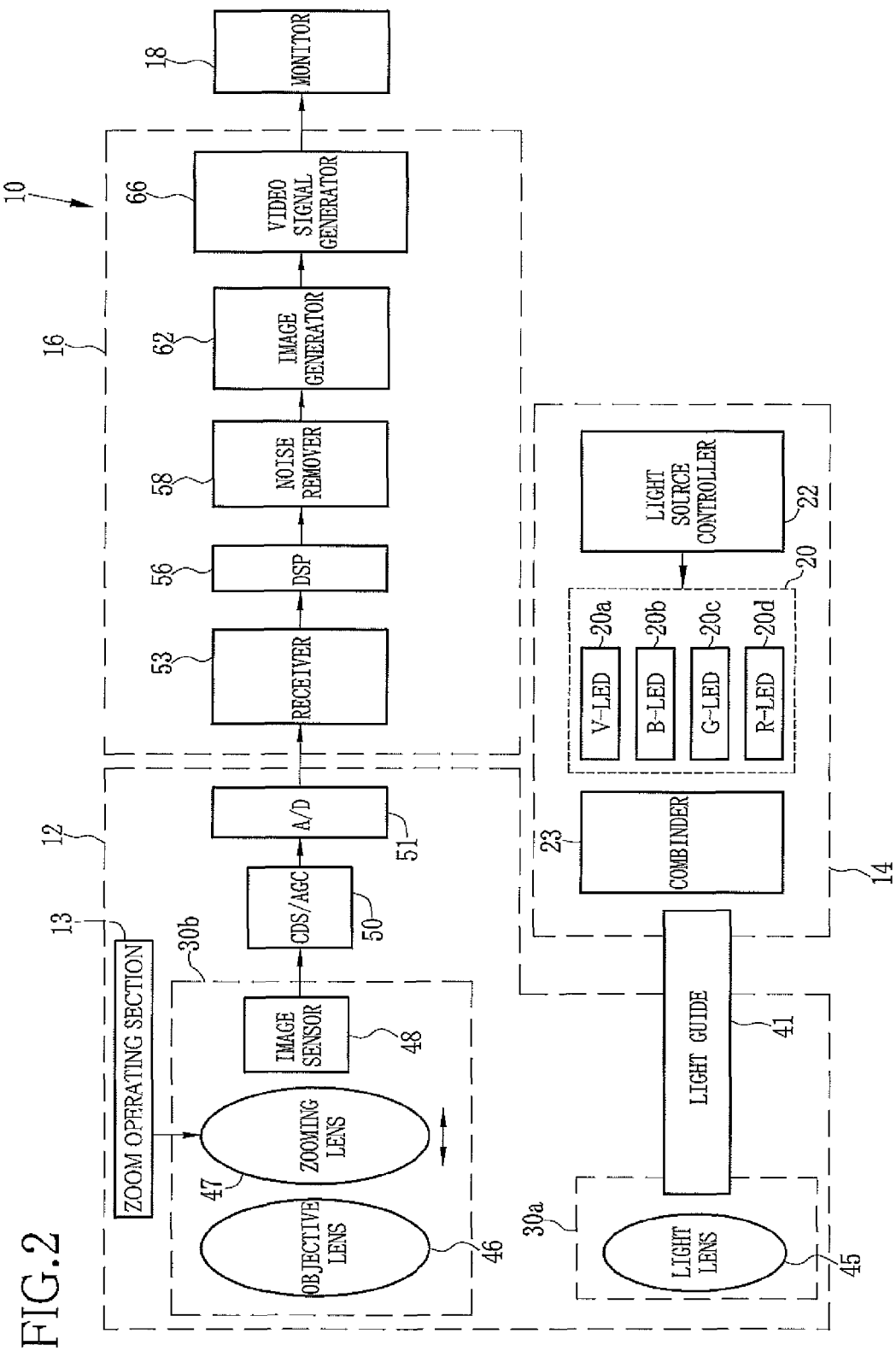
FIG. 2 is a block diagram illustrating functions of the endoscope system.

As illustrated in FIG. 2, the light source device 14 generates illumination light, which is applied to an object of interest. The light source device 14 comprises a light source unit 20, a light source controller 22, and a light path combiner (hereinafter simply referred to as the combiner) 23. The light source unit 20 comprises two or more light sources. The light source controller 22 controls each light source of the light source unit 20. The combiner 23 combines the light paths of the light from the light source unit 20 with each other.

The light source unit 20 comprises LEDs (light emitting diodes) of four colors: a violet LED (hereinafter abbreviated as V-LED) 20a, a blue LED (hereinafter abbreviated as B-LED) 20b, a green LED (hereinafter abbreviated as G-LED) 20c, and a red LED (hereinafter abbreviated as R-LED) 20d.

Figure 3:
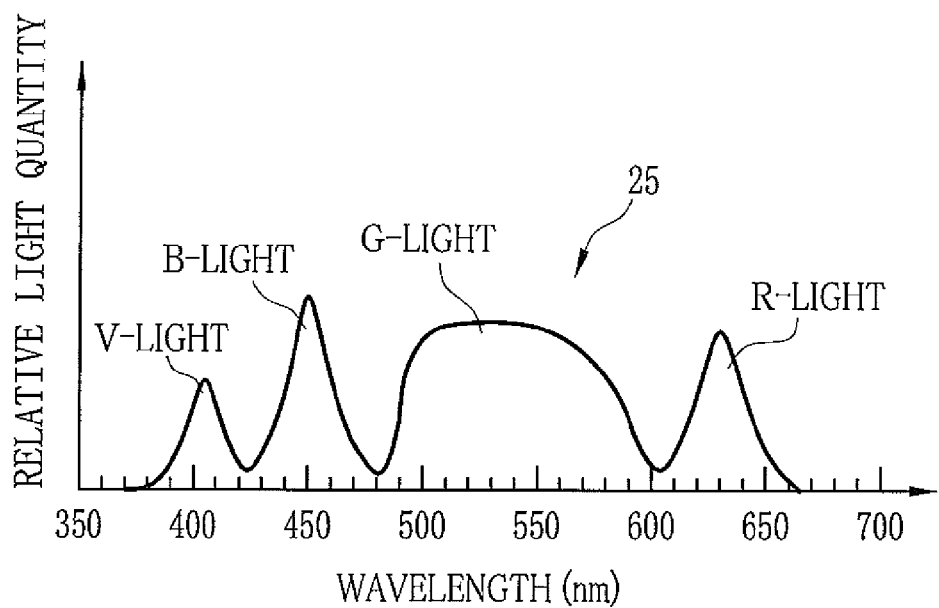
FIG. 3 is a graph illustrating a spectrum of multicolor spectrum light.

As illustrated in FIG. 3, the V-LED 20a is a violet light source that emits violet light beams (hereinafter abbreviated as V-light) in a wavelength range of 380 to 420 nm and having the center wavelength of 405 nm. The B-LED 20b is a blue light source that emits blue light beams (hereinafter abbreviated as B-light) in a wavelength range of 420 to 500 nm and having the center wavelength of 460 nm. The G-LED 20c is a green light source that emits green light beams (hereinafter abbreviated as G-light) in a wavelength range of 480 to 600 nm. The R-LED 23d is a red light source that emits red light beams (hereinafter abbreviated as R-light) in a wavelength range of 600 to 650 nm and having the center wavelength in a range of 620 to 630 nm. Note that each center wavelength of the V-light from the V-LED 20a and the B-light from the B-LED 20b has a width in the order of ±5 nm to ±10 nm.

Figure 4:
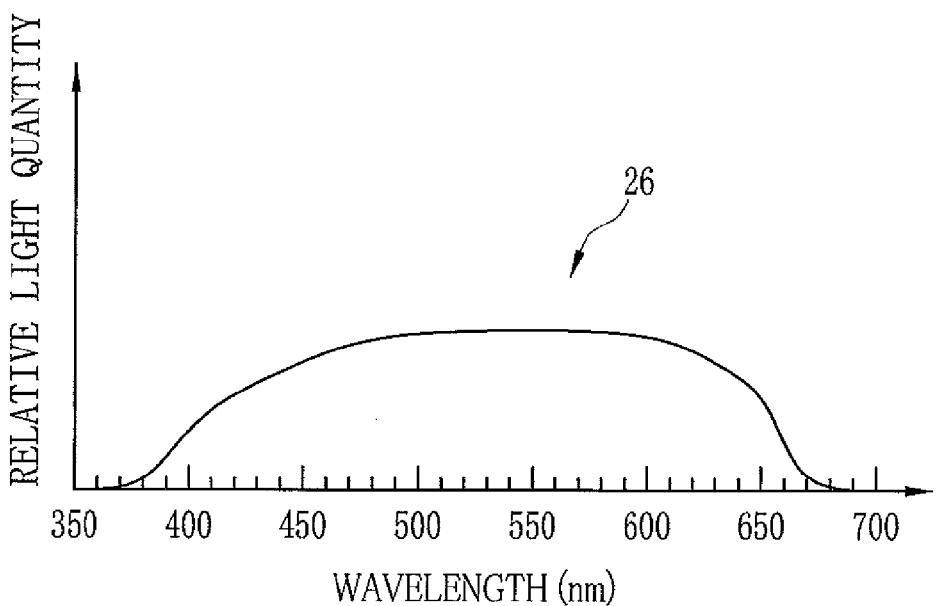
FIG. 4 is a graph illustrating a spectrum of continuous-spectrum light from a xenon lamp.

The light source unit 20, which is comprised of the multiple light sources that independently emit light of different colors, emits multicolor spectrum light 25 having a multicolor spectrum, into which the V-light, the B-light, the G-light, and the R-light are combined. The emission light quantity (hereinafter simply referred to as the light quantity) of each of the LEDs 20a to 20d is controlled independently. The optical spectrum (hereinafter simply referred to as the spectrum) of the multicolor spectrum light 25 is changed by changing at least one of the light quantities of the light from the LEDs 20a to 20d. In this embodiment, the light source unit 20 emits the V-light, the B-light, the G-light, and the R-light with the distribution (or balance) emulating that of white broadband continuous-spectrum light 26 (see FIG. 4), which is emitted as the illumination light from a xenon lamp used by a conventional endoscope system. This mode is referred to as xenon emulation mode. The multicolor spectrum light 25 emitted from the light source unit 20 in the xenon emulation mode is referred to as the first multicolor spectrum light.

The light source controller 22 independently controls drive current and drive voltage applied to each of the LEDs 20a to 20d of the light source unit 20 and a pulse width and pulse length of pulses used for inputting the drive current and drive voltage to the LEDs 20a to 20d. Thereby, the light source controller 22 controls the emission timing and the light quantity of the light emitted from each of the LEDs 20a to 20d. To be more specific, the light source controller 22 controls each of the LEDs 20a to 20d of the light source unit 20 to generate the first multicolor spectrum light, into which the V-light, the B-light, the G-light, and the R-light from the LEDs 20a to 20d are combined. In the case where the first multicolor spectrum light is generated, the light source controller 22 controls the emission timing and the light quantities of the LEDs 20a to 20d to make an integral of the light quantity (hereinafter referred to as the light quantity integral) of the first multicolor spectrum light in a first wavelength band equal to a light quantity integral of the continuous-spectrum light in the first wavelength band and to make a light quantity integral of the first multicolor light in a second wavelength band equal to a light quantity integral of the continuous-spectrum light in the second wavelength band.

The light quantity integral is a value obtained by integrating a relative light quantity at each wavelength in a predetermined wavelength range (e.g. the first wavelength band, the second wavelength band, or the like) over the predetermined wavelength range. In this embodiment, the light quantity integral is a value obtained by integrating a relative light quantity of the light emitted from the light source unit 20 over a specific wavelength band. In view of the losses during the light propagation, the light quantity integral may be a value obtained by integrating a relative light quantity of the light to be applied to the object over the specific wavelength band. A relative light quantity at each wavelength of light (that is, the light reflected from the object or a phantom emulating the object) incident on the image sensor 48 may be integrated over the specific wavelength band to obtain the light quantity integral. In a case where a pixel in the image sensor 48 is provided with a color filter, a relative light quantity of the light (that is, the light reflected from the object or the phantom emulating the object and passed through the color filter, in other words, the light to be photoelectrically converted in the pixel of the image sensor 48) at each wavelength may be integrated over the specific wavelength band to obtain the light quantity integral. The above-described light quantity integrals are the values functioning substantially the same in the actual endoscope system, in which the properties of the LEDs 20a to 20d, the losses during the light propagation, and the sensitivity of the image sensor 48 (including the characteristics of the color filters), and the like are predetermined.

The continuous-spectrum refers to a spectrum of light having or including at least a part of the wavelength band (wavelength range) of the light emitted from a white light source. The continuous-spectrum light refers to light having a continuous spectrum. The white light source refers to a light source that emits light of the distribution with gradually changing values across the visible range (e.g. from 400 nm to 700 nm). To be more specific, the white light source may be a xenon lamp, a halogen lamp, a white LED, or the like. The light including at least a part of the wavelength band of the light from the white light source refers to light extracted by a color filter or the like from the light emitted from the white light source.

The multicolor spectrum refers to one spectrum in which the spectrums of the light from the two or more light sources are combined with each other. The multicolor spectrum light refers to the light in which the light from the two or more light sources are combined with each other. Here, the term "broadband" means that the wavelength range of light is wider (broader) than the wavelength range of the light from at least one of the light sources (the LEDs 20a to 20d) used in the light source unit 20. For example, the wavelength range (wavelength band) of white light from the xenon lamp is wider than each of a wavelength band (violet wavelength range) of the V-light from the LED 20a, a wavelength band (blue wavelength range) of the B-light from the LED 20b, a wavelength band (green wavelength range) of the G-light from the LED 20c, and a wavelength band (red wavelength range) of the R-light from the LED 20d, and includes all the wavelength components of all the wavelength bands (that is, the wavelength range greater than or equal to 350 nm and less than 700 nm), and has the distribution gradually changing values over the visible range. Thus, the white light from the xenon lamp is the broadband continuous-spectrum light 26. The broadband continuous-spectrum light is not limited to the white light from the xenon lamp and includes the white light and the like used in the conventional endoscope systems.

The first wavelength band is a predetermined specific wavelength range. The second wavelength band is a predetermined wavelength range. The second wavelength band is different from the first wavelength band. The first wavelength band and the second wavelength band are determined freely excluding the case where the first and second wavelength bands are completely identical. For example, the first wavelength band may partly overlap the second wavelength band. One of the first wavelength band and the second wavelength band may be entirely included by the other, for example, at least a boundary of the first wavelength band is different from that of the second wavelength band but the first wavelength band (or the second wavelength band) constitutes a part of the second wavelength band (or the first wavelength band). In this embodiment, the first wavelength band is a wavelength range greater than or equal to 350 nm and less than 480 nm including the violet wavelength range and the blue wavelength range. The second wavelength band is the green wavelength range, that is, a wavelength range greater than or equal to 480 nm and less than 600 nm. A third wavelength band is the red wavelength range, that is, a wavelength range greater than or equal to 600 nm and less than 700 nm.

The light source controller 22 controls the balance among the light quantities of the respective LEDs 20a to 20d of the light source unit 20 to generate the first multicolor spectrum light as described above. The object observed under the illumination of the first multicolor spectrum light through the endoscope system 10 is comparable to (looks similar to or is able to be compared with) that observed under the illumination of the white light from the xenon lamp.

The multicolor spectrum light (the first multicolor spectrum light) from the light source unit 20 is incident on a light guide 41, which extends through the insertion section 12a, through the combiner 23. The light guide 41 is incorporated in the endoscope 12 and a universal cord, which connects the endoscope 12 to the light source device 14 and the processor device 16. The light guide 41 transmits the illumination light emanated from the combiner 23 to the distal portion 12d of the endoscope 12. Note that a multimode fiber may be used as the light guide 41. For example, a small-diameter fiber cable with the core diameter 105 μm, the clad diameter 125 μm, and the outer diameter φ 0.3 to 0.5 mm (including a protection layer (jacket)) may be used.

The distal portion 12d of the endoscope 12 comprises an illumination optical system 30a and an imaging optical system 30b. The illumination optical system 30a has a light lens 45. The illumination light transmitted through the light guide 41 is applied to the object through the light lens 45. The imaging optical system 30b has an objective lens 46, a zooming lens 47, and an image sensor 48. The light (the reflection light, the light including fluorescence emanating from the object, and the like) reflected from the object is incident on the image sensor 48 through the objective lens 46 and the zooming lens 47. Thereby an image of the object is formed on the image sensor 48. Note that the zooming lens 47 is movable between the telephoto end and the wide angle end by operating the zoom operating section 13b, to magnify or reduce the size of the image of the object formed on the image sensor 48.

The image sensor 48 is a color image sensor. The image sensor 48 comprises pixels of two or more colors, which are sensitive to light of respective colors. The image sensor 48 captures an image of the light reflected from the object and thereby outputs image signals. It is preferred that the image sensor 48 is a CCD (Charge Coupled Device) image sensor, a CMOS (Complementary Metal-Oxide Semiconductor) image sensor, or the like. In the image sensor 48, each pixel is provided with one of an R (red) color filter, a G (green) color filter, a B (blue) color filter. The image sensor 48 captures the image of the light reflected from the object and thereby outputs the image signals of the respective colors (R, G, and B). In other words, the image sensor 48 has R (red) pixels provided with the R color filters, G (green) pixels provided with the G color filters, and B (blue) pixels provided with the B color filters, and each pixel outputs an image signal of the corresponding color. Thereby, the image sensor 48 outputs RGB image signals.

To be more specific, the object is irradiated with the first multicolor spectrum light, so that the B pixel of the image sensor 48 receives the reflected V-light and the reflected B-light of the first multicolor spectrum light and outputs a blue image signal (hereinafter referred to as the B-image signal). The G pixel of the image sensor 48 receives the reflected G-light of the first multicolor spectrum light and outputs a green image signal (hereinafter referred to as the G image signal). The R pixel of the image sensor 48 receives the reflected R-light of the first multicolor spectrum light and outputs a red image signal (hereinafter referred to as the R image signal).

A complementary color image sensor with complementary color filters of C (cyan), M (magenta), Y (yellow), and G (green) may be used instead of the image sensor 48, which is the color image sensor of primary colors. In the case where the complementary color image sensor is used, CMYG image signals of four colors (CMYG) are outputted. The CMYG image signals of four colors are converted into the RGB image signals of three colors through complementary color-primary color conversion. Thereby the RGB image signals similar to or the same as those generated by the image sensor 48 are obtained. A monochrome sensor with no color filters may be used instead of the image sensor. In this case, the light source controller 22 emits the V-light, the B-light, the G-light, and the R-light in a time-division manner as necessary. The V-light and the B-light may be emitted simultaneously because both the V-light and the B-light are received by the B pixel.

The image signal outputted from the image sensor 48 is transmitted to a CDS/AGC circuit 50. The CDS/AGC circuit 50 performs correlated double sampling (CDS) and automatic gain control (AGC) on the image signal that is an analog signal. The image signal that is outputted from the CDS/AGC circuit 50 is then converted into a digital image signal by an A/D converter 51. After the A/D conversion, the digital image signal is inputted to the processor device 16.

The processor device 16 comprises a receiver 53, a DSP (Digital Signal Processor) 56, a noise remover 58, an image generator 62, and a video signal generator 66.

The receiver 53 receives the digital RGB image signals from the endoscope 12. The DSP 56 performs various types of signal processing on the received RGB image signals such as defect correction processing, offset processing, gain correction process, linear matrix processing, gamma conversion process, and demosaicing process. In the defect correction processing, a signal of a defective pixel in the image sensor 48 is corrected. In the offset processing, dark current components are removed from the RGB image signals that have been subjected to the defect correction processing. Thereby an accurate zero level is set. In the gain correction process performed after the offset processing, a signal level is adjusted or corrected by multiplying the RGB image signals by a specific gain. After the gain correction process, the RGB image signals are subjected to the linear matrix processing to increase color reproducibility. Thereafter, brightness and saturation are adjusted or corrected through the gamma conversion process. After the linear matrix processing, the demosaicing process (also referred to as equalization process or synchronization process) is performed to generate signal (s) of color (s) lacking in each pixel through interpolation. Owing to the demosaicing process, each pixel has three colors (RGB) of signals.

The noise remover 58 performs a noise removing process (for example, a moving average method or a median filter method) on the RGB image signals that have been subjected to the demosaicing process and the like performed by the DSP 56. The image signal from which the noise has been removed is transmitted to the image generator 62.

The image generator 62 performs a color conversion process, a color enhancement process, and a structure enhancement process on the RGB image signals to generate an image (hereinafter may referred to as endoscopic image). The color conversion process is performed on the RGB image signals through 3×3 matrix processing, a tone conversion process, a three-dimensional LUT (lookup table) process, or the like. The color enhancement process is performed on the RGB image signals that have been subjected to the color conversion process. The structure enhancement process is to enhance the structure of the object (e.g. surface blood vessels, pit patterns, or the like). The structure enhancement process is performed on the RGB image signals after the color enhancement process. As described above, for example, the endoscopic image is a color image produced from the RGB image signals that have been subjected to the various types of image processing all the way up to the structure enhancement process. The video signal generator 66 converts the endoscopic image, which is generated by the image generator 62, into a video signal to be displayed as an image on the monitor 18. Based on the video signal, the monitor 18 displays the endoscopic image.

Next, the characteristics of the first multicolor spectrum light are described. In the xenon emulation mode, the endoscope system 10 according to this embodiment uses the first multicolor spectrum light 27 as the illumination light. The first multicolor spectrum light 27 is obtained by emitting the V-light, the B-light, the G-light, and the R-light with the distribution of the relative light quantities shown in FIG. 5 and combining the V-light, the B-light, the G-light, and the R-light with one another. In FIG. 5, there is a significant difference in shape of the spectrum between the first multicolor spectrum light 27 and the continuous-spectrum light 26 of the xenon lamp depicted by a chain and double-dashed line. The shape of the spectrum of the first multicolor spectrum light 27 is not identical to the shape of the spectrum of the continuous-spectrum light 26 of the xenon lamp. This is partly because there are only four LEDs in the light source unit 20 and the continuous-spectrum light 26 of the xenon lamp cannot be completely reproduced only by adjusting the light quantities of the V-light, the B-light, the G-light, and the R-light, but this is mainly because the object under the illumination of the first multicolor spectrum light 27 is observed in a comparable manner to (in other words, the object looks similar to or is able to be compared with) the object observed under the illumination of the continuous-spectrum light 26 of the xenon lamp even if the first multicolor spectrum light 27 does not completely reproduce the shape of the spectrum of the continuous-spectrum light 26 of the xenon lamp.

The light source controller 22 controls the light quantities of the respective LEDs 20a to 20d of the light source unit 20 such that the first multicolor spectrum light 27 emulates the continuous-spectrum light 26 of the xenon lamp, without completely reproducing the shape of the spectrum of the continuous-spectrum light 26. To be more specific, as illustrated in FIG. 6, the light source controller 22 controls the light quantities of the respective LEDs 20a to 20d to make the light quantity integral of the first multicolor spectrum light 27 equal to the light quantity integral of the continuous-spectrum light 26 of the xenon lamp in each of the first wavelength band (the blue wavelength range), the second wavelength band (the green wavelength range), and the third wavelength band (the red wavelength range). In other words, the light source controller 22 makes a light quantity integral $S1_E$ of the first multicolor spectrum light 27 in the first wavelength band, which is to be applied to the object (or emitted from the light source unit 20), equal to a light quantity integral $S1_X$ of the continuous-spectrum light 26 of the xenon lamp in the first wavelength band ($S1_E \approx S1_X$) and makes the light quantity integral $S2_E$ of the first multicolor spectrum light 27 in the second wavelength band equal to the light quantity integral $S2_X$ of the continuous-spectrum light 26 of the xenon lamp in the second wavelength band ($S2_E \approx S2_X$). Furthermore, in this embodiment, the light source controller 22 makes a light quantity integral $S3_E$ of the first multicolor spectrum light 27 in the third wavelength band equal to a light quantity integral $S3_X$ of the continuous-spectrum light 26 of the xenon lamp in the third wavelength band ($S3_E \approx S3_X$).

As described above, with the use of the first multicolor spectrum light 27 whose light quantity integral equals that of the continuous-spectrum light 26 of the xenon lamp in each of the first wavelength band, the second wavelength band, and the third wavelength band, an image of the object observed under the illumination of the first multicolor spectrum light 27 is comparable to (looks similar to or is able to be compared with) an image of the object observed under the illumination of the continuous-spectrum light 26 of the xenon lamp even if the shape of the spectrum of the first multicolor spectrum light 27 does not coincide with the shape of the spectrum of the continuous-spectrum light 26 of the xenon lamp.

In the first embodiment, note that the light quantity integral of the first multicolor spectrum light 27 equals (coincides with) the light quantity integral of the continuous-spectrum light 26 of the xenon lamp in each of the first wavelength band, the second wavelength band, and the third wavelength band, which is the red wavelength range. However, in the case where the light quantity integral of the first multicolor spectrum light 27 equals the light quantity integral of the continuous-spectrum light 26 of the xenon lamp in at least the first and second wavelength bands, an image of the object observed under the illumination of the first multicolor spectrum light 27 is comparable to an image of the object observed under the illumination of the continuous-spectrum light 26 of the xenon lamp. This is because the light in the first and second wavelength bands contains most of the information of the tissue or the structure (e.g. blood vessels, the pit patterns, or the like) that is an important index for diagnosis in the endoscopic image. The light in the third wavelength band contains substantially none of such information. Hence it can be said that the continuous-spectrum light 26 of the xenon lamp is substantially emulated by the first multicolor spectrum light 27 in the case where the blood vessels or the like observed under illumination of the first multicolor spectrum light 27 is comparable to those observed under the illumination of the continuous-spectrum light 26 of the xenon lamp.

In the first embodiment, the light quantity integral $S1_E$ of the first multicolor spectrum light 27 in the first wavelength band equals the light quantity integral $S1_X$ of the continuous-spectrum light 26 of the xenon lamp in the first wavelength band. Since the first multicolor spectrum light 27 in the first wavelength band is mainly composed of the V-light and the B-light, the balance (distribution) between the light quantity of the V-light and the light quantity of the B-light may be changed while the light quantity integral $S1_E$ of the first multicolor spectrum light 27 in the first wavelength band is maintained unchanged. It is preferred to adjust the balance between the light quantity of the V-light and the light quantity of the B-light such that the spectrum of the V- and B-light emulates or resembles the spectrum of the continuous-spectrum light 26 of the xenon lamp as much as possible at least in the first wavelength band. To be more specific, it is preferred to make the light quantity of the V-light less than the light quantity of the B-light in accordance with the decrease in the light quantity of the continuous-spectrum light 26 of the xenon lamp in the first wavelength band toward the short wavelength side. It is preferred to set the light quantity of the V-light such that the shape of the spectrum of the V-light on the short-wavelength side emulates or resembles the shape of the spectrum of the continuous-spectrum light 26 as much as possible. Then, it is preferred to set the light quantity of the B-light based on the set light quantity of the V-light and the light quantity integral $S1_X$ of the continuous-spectrum light 26 of the xenon lamp in the first wavelength band. Thereby the object observed under the illumination of the first multicolor spectrum light 27 looks similar to that observed under the illumination of the continuous-spectrum light 26 of the xenon lamp.

Since the first multicolor spectrum light 27 in the first wavelength band is mainly composed of the light of the two colors (that is, the V-light and the B-light), the first wavelength band may be separated into two wavelength bands, a first short-wavelength band and a first long-wavelength band. The first short-wavelength band is a short-wavelength side component of the first wavelength band and includes the wavelength band of the V-light. The first long-wavelength band is a long-wavelength side component of the first wavelength band and includes the wavelength band of the B-light. In this case, a light quantity integral of the first multicolor spectrum light 27 in the first short-wavelength band is made equal to a light quantity integral of the continuous-spectrum light 26 of the xenon lamp in the first short-wavelength band, and a light quantity integral of the first multicolor spectrum light 27 in the first long-wavelength band is made equal to a light quantity integral of the continuous-spectrum light 26 of the xenon lamp in the first long-wavelength band. Thereby the light quantity integral $S1_E$ of the first multicolor spectrum light 27 in the first wavelength band equals (coincides with) the light quantity integral $S1_X$ of the continuous-spectrum light 26 of the xenon lamp in the first wavelength band.

Figure 7:
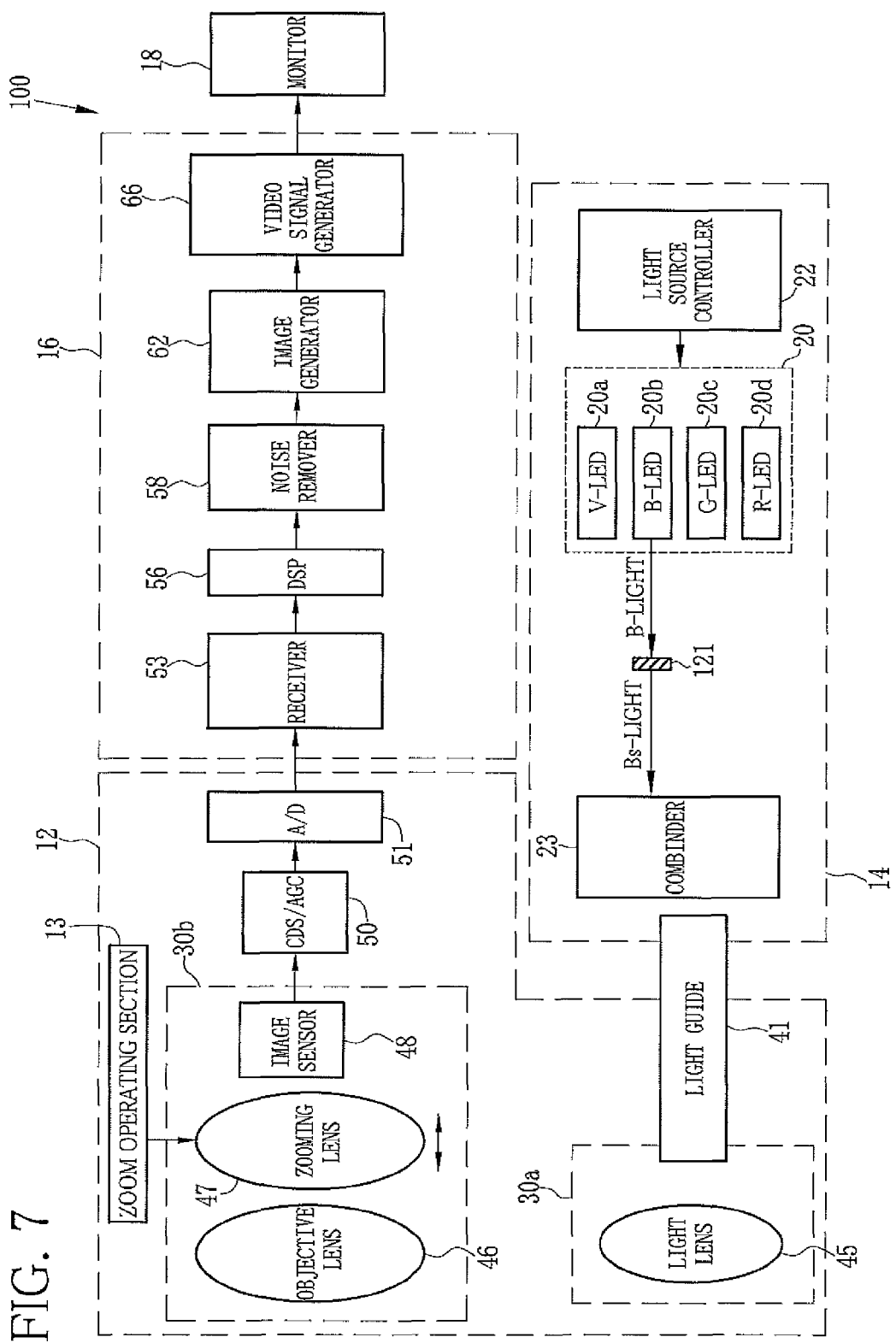
FIG. 7 is a block diagram illustrating an endoscope system provided with a band limiter.

In the first embodiment, note that the B-light from the B-LED 20b is used as the first multicolor spectrum light 27. However, the light in the wavelength range from approximately 450 nm to approximately 500 nm reduces the contrast of the structure such as the surface blood vessels and the pit patterns. To prevent this, a band limiter 121 is provided in the light path of the light from the B-LED 20b in an endoscope system 100 illustrated in FIG. 7, by way of example. The band limiter 121 reduces or eliminates the light in the wavelength range from approximately 450 nm to approximately 500 nm. Thereby Bs-light is generated by reducing or eliminating the wavelength component of approximately 450 nm to approximately 500 nm from the B-light emitted from the B-LED 20b. It is preferred to use the Bs-light as the first multicolor spectrum light 27. In this case, the light quantity integral in the first wavelength band may be calculated based on the B-light emitted from the B-LED 20b. The light quantity integral in the first wavelength band may be calculated based on the Bs-light that passed through the band limiter 121.

Note that the light quantity integral $S1_E$ of the first multicolor spectrum light 27 in the first wavelength band has a tolerance in the order of at least 5% to 10% relative to the light quantity integral $S1_X$ of the continuous-spectrum light 26 of the xenon lamp in the first wavelength band. The light quantity integral $S2_E$ of the first multicolor spectrum light 27 in the second wavelength band has a tolerance in the order of at least 5% to 10% relative to the light quantity integral $S2_X$ of the continuous-spectrum light 26 of the xenon lamp in the second wavelength band. The light quantity integral $S3_E$ of the first multicolor spectrum light 27 in the third wavelength band has a tolerance in the order of at least 5% to 10% relative to the light quantity integral $S3_X$ of the continuous-spectrum light 26 of the xenon lamp in the third wavelength band. Since the sense of sight is relatively insensitive to a difference in color, the object observed under the illumination of the first multicolor spectrum light 27 is comparable to (or looks similar to) that observed under the continuous-spectrum light 26 of the xenon lamp in the case where the tolerances are within the above-described range. In other words, the light quantity integral of the first multicolor spectrum light 27 is regarded as equal to that of the continuous-spectrum light 26. Hence, throughout this specification, the light quantity integrals being "equal (or being coincident with each other)" include those being "substantially equal", including the above-described tolerance.

Second Embodiment

In the first embodiment, the light source controller 22 allows the LEDs 20a to 20d of the light source unit 20 to generate the first multicolor spectrum light 27, which emulates the continuous-spectrum light 26 of the xenon lamp. Instead of the first multicolor spectrum light 27, the light source controller 22 may allow the LEDs 20a to 20d of the light source unit 20 to generate second multicolor spectrum light having a second multicolor spectrum different from those of the first multicolor spectrum light 27 and the continuous-spectrum light 26.

Figure 8:
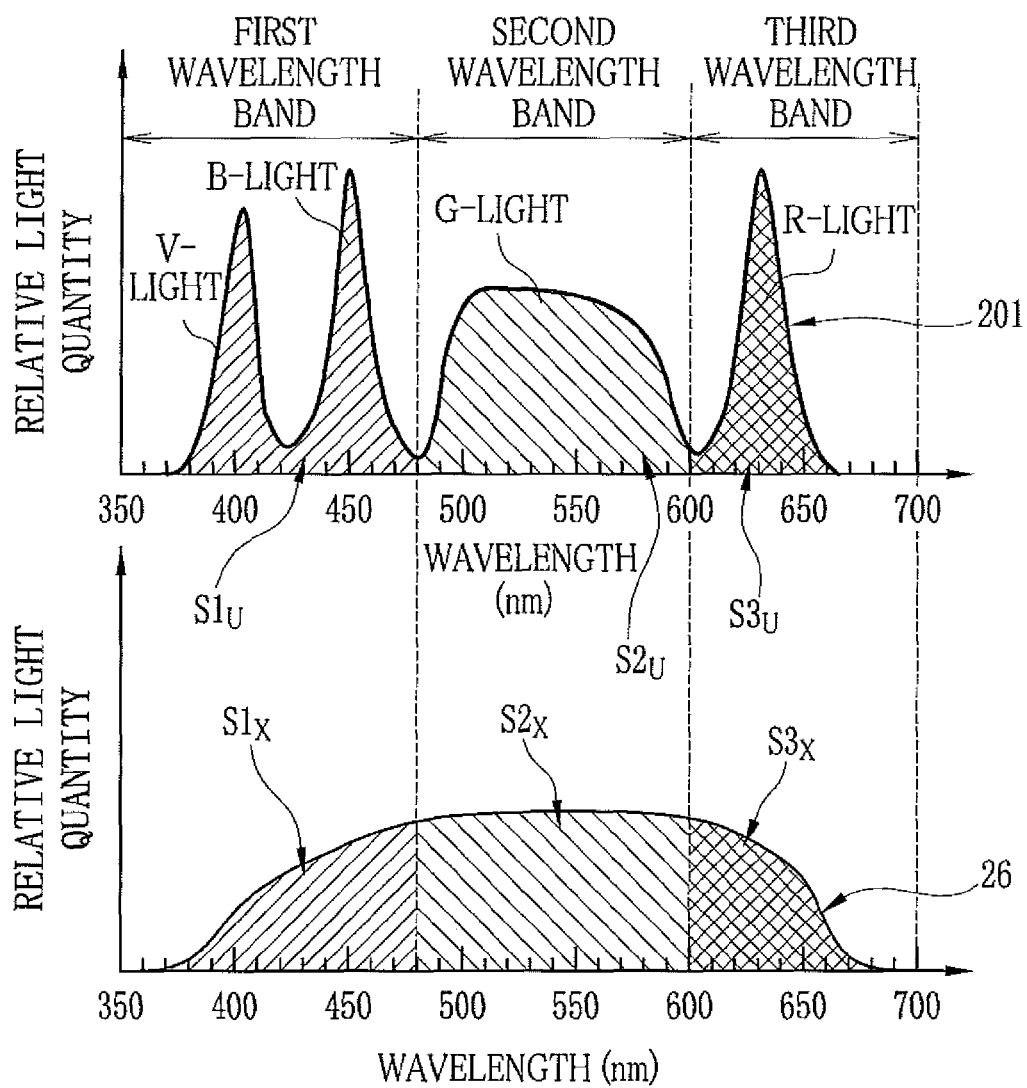
FIG. 8 is an explanatory view illustrating a relationship between second multicolor spectrum light and the continuous-spectrum light from the xenon lamp.

The second multicolor spectrum light is illumination light having a specific spectrum different from that of the light from the xenon lamp in the conventional endoscope system and illuminates the object of interest. For example, as illustrated in FIG. 8, the light source controller 22 makes a light quantity integral $S1_U$ of second multicolor spectrum light 201 in the first wavelength band greater than the light quantity integral $S1_X$ of the continuous-spectrum light 26 from the xenon lamp in the first wavelength band ($S1_U > S1_X$) and makes a light quantity integral $S2_U$ of the second multicolor spectrum light 201 in the second wavelength band equal to the light quantity integral $S2_X$ of the continuous-spectrum light 26 from the xenon lamp in the second wavelength band ($S2_U \approx S2_X$). Furthermore, in this embodiment, the light source controller 22 makes a light quantity integral $S3_U$ of the second multicolor spectrum light 201 in the third wavelength band equal to the light quantity integral $S3_X$ of the continuous-spectrum light 26 from the xenon lamp in the third wavelength band ($S3_U \approx S3_X$).

The blood vessels or the pit patterns in the mucosal surface layer are observed more clearly in the case where the object is observed under the illumination of the above-described second multicolor spectrum light 201 than in the case where the object is observed under the illumination of the continuous-spectrum light 26 of the xenon lamp because the light quantity integral of the second multicolor spectrum light 201 in the first wavelength band, which has a high amount of the information about the blood vessels and the pit patterns in the mucosal surface layer, is greater than that of the continuous-spectrum light 26 of the xenon lamp in the first wavelength band. In the case where the illumination light is selectable between the first multicolor spectrum light 27 and the second multicolor spectrum light 201, each multicolor spectrum light brings about advantages described above.

Each of the first multicolor spectrum light 27 and the second multicolor spectrum light 201 according to an aspect of the present invention is selectable by operating a mode selection switch (not shown) or the like provided in the control handle unit 12b of the endoscope 12. In particular, it is preferred to automatically select one of the first multicolor spectrum light 27 and the second multicolor spectrum light 201 in accordance with the model of the endoscope 12 used in the endoscope system 10.

Figure 9:
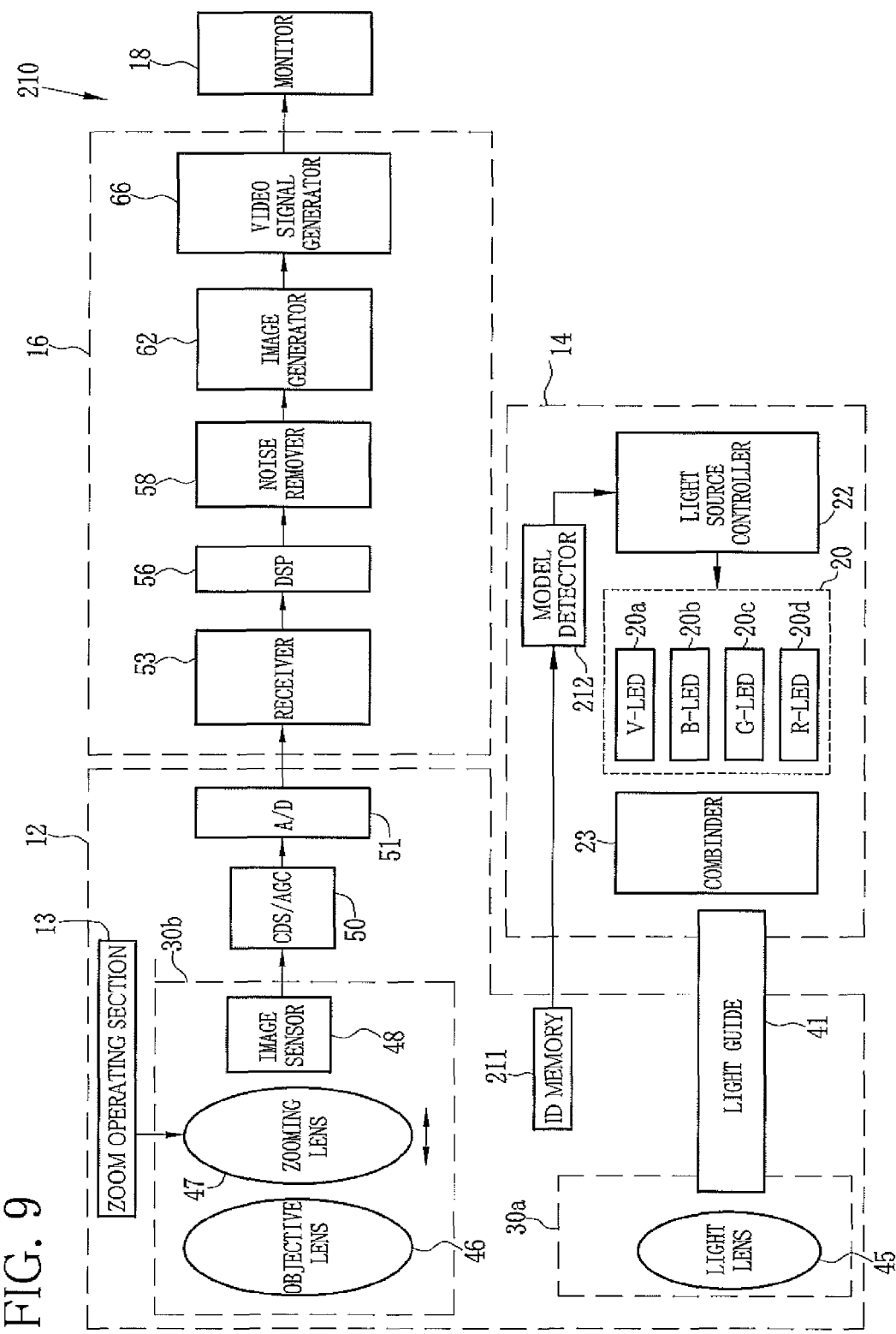
FIG. 9 is a block diagram of an endoscope system that switches between the first multicolor spectrum light and the second multicolor spectrum light according to the model of an endoscope.

As illustrated in FIG. 9, an ID memory 211 is provided in the endoscope 12 and a model detector 212 is provided in the light source device 14 in the case where one of the first multicolor spectrum light 27 and the second multicolor spectrum light 201 is automatically selected in accordance with the model of the endoscope 12 in an endoscope system 210. The ID memory 211 stores ID (Identification Data), which identifies the model of the endoscope 12. In the case where the endoscope 12 is connected to the light source device 14, the model detector 212 reads out the ID of the endoscope 12 from the ID memory 211 to detect the model of the endoscope 12 and inputs a result of the detection to the light source controller 22. The light source controller 22 selects one of the first multicolor spectrum light 27 and the second multicolor spectrum light 201 to be generated in the light source unit 20 in accordance with the model (of the endoscope 12) detected by the model detector 212. To be more specific, in the case where the model of the endoscope 12 is the one used in the conventional endoscope system using the continuous-spectrum light of the xenon lamp, it is preferred that the light source controller 22 automatically sets the first multicolor spectrum light 27 as the illumination light to be generated in the light source unit 20. In the case where the model of the endoscope 12 is other than the one described above (in other words, in the case where the model of the endoscope 12 is the one used only in the endoscope system using the multicolor spectrum light or the like), it is preferred that the light source controller 22 automatically sets the second multicolor spectrum light 201 as the illumination light to be generated in the light source unit 20.

In a case where an endoscope for the conventional endoscope system using the xenon lamp is connected, doctors expect that an object is observed in a manner similar to (or looks similar to the object observed through) the conventional endoscope system to which they have been accustomed. In a case where an endoscope for the endoscope system using the multicolor spectrum light as the illumination light is connected, the doctors expect the observation that makes full use of the advantages of the multicolor spectrum light. By automatically selecting one of the first multicolor spectrum light 27 and the second multicolor spectrum light 201 in accordance with the model of the endoscope 12 as described above, the endoscopic image that meets the need of the doctors is automatically provided without operation or settings. Furthermore, it is preferred to automatically set the illumination light in accordance with the model of the endoscope 12 in a default setting, and then to allow a doctor to manually select the illumination light based on the doctor's determination.

Figure 10:
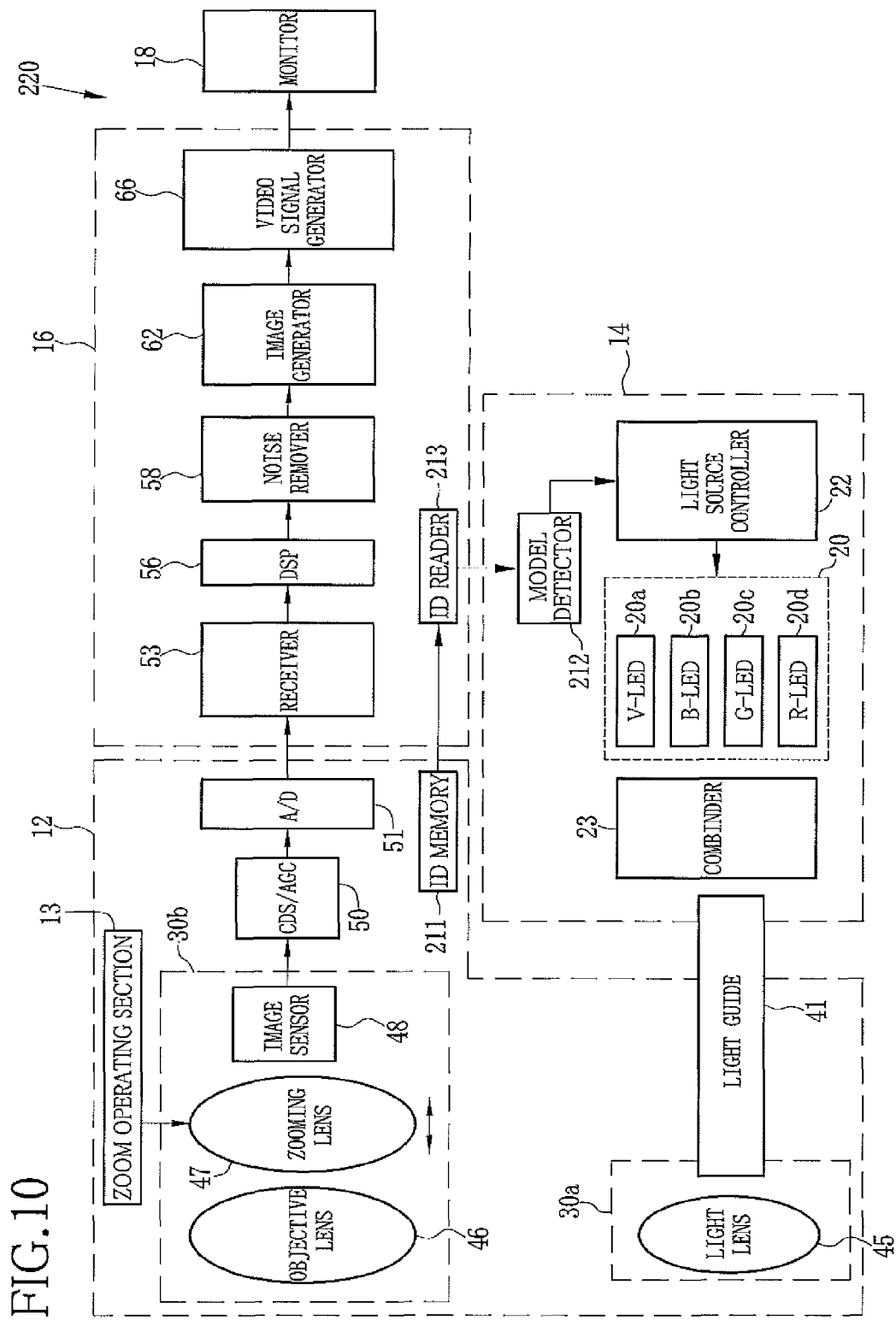
FIG. 10 is a block diagram of an endoscope system that switches between the first multicolor spectrum light and the second multicolor spectrum light according to the model of the endoscope.

In the endoscope system 210 illustrated in FIG. 9, the light source device 14 uses the model detector 212 to detect the connection of the endoscope 12, and the model detector 212 reads out the ID from the endoscope 12 to detect the model of the endoscope 12. In an endoscope system 220 illustrated in FIG. 10 by way of example, an ID reader 213 is provided in the processor device 16. The ID reader 213 detects the connection of the endoscope 12 and reads out the ID from the endoscope 12. In this case, the model detector 212 obtains the ID of the endoscope 12 from the ID reader 213 of the processor device 16, to detect the model of the endoscope 12.

Third Embodiment

Figure 11:
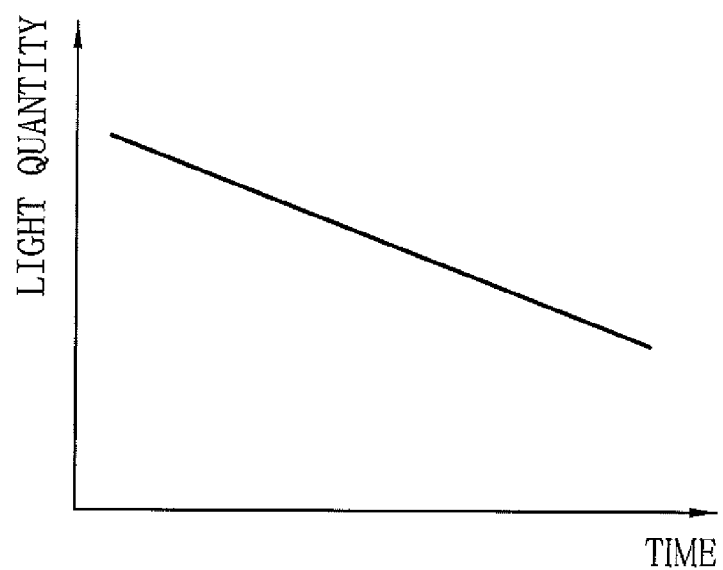
FIG. 11 is a graph illustrating aging of a semiconductor light source.

A semiconductor light source such as the LED has longer life than a conventional light source such as the xenon lamp. However, the semiconductor light source such as the LED deteriorates (or ages) with time as illustrated in FIG. 11. Due to aging, the light quantity may be reduced even if the semiconductor light source is driven by a specified current or voltage. The degree of aging varies according to the type (e.g. the wavelengths of the light emitted from the semiconductor light source) of the semiconductor light source. In the case where the aging of the semiconductor light source proceeds, for example, the multicolor spectrum light generated based on the predetermined control by the light source controller 22 may not meet the requirements of the first multicolor spectrum light 27. To prevent this, it is preferred that the light source controller 22 controls the emissions of the first multicolor spectrum light 27 and the second multicolor spectrum light 201 in view of the aging of the LEDs 20a to 20d of the light source unit 20.

Figure 12:
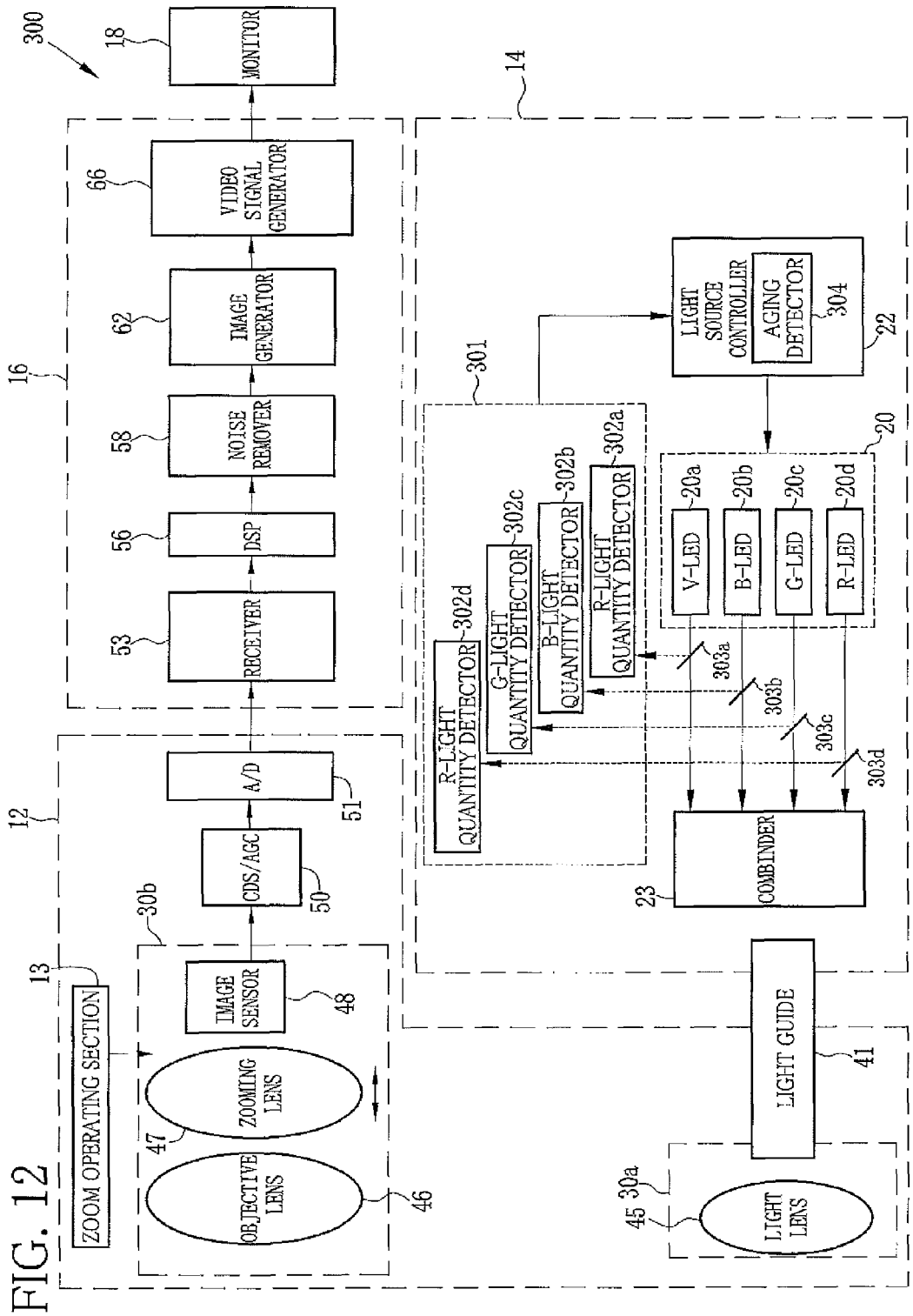
FIG. 12 is a block diagram illustrating an endoscope system that emits the first multicolor spectrum light corresponding to the aging of the semiconductor light source.

To generate the first multicolor spectrum light 27 or the second multicolor spectrum light 201 that meets the requirements described in the first or second embodiment despite the chronological deterioration of the LEDs 20a to 20d of the light source unit 20, the light source device 14 is provided with a light quantity detector 301 and the light source controller 22 is provided with an aging detector 304 in an endoscope system 300 illustrated in FIG. 12, by way of example.

The light quantity detector 301 comprises a V-light quantity detector 302a for detecting the light quantity of the V-LED 20a, a B-light quantity detector 302b for detecting the light quantity of the B-LED 20b, a G-light quantity detector 302c for detecting the light quantity of the G-LED 20c, and an R-light quantity detector 302d for detecting the light quantity of the R-LED 20d. The V-light quantity detector 302a obtains a part of the V-light through a mirror 303a to detect the light quantity of the V-light emitted from the V-LED 20a. The mirror 303a is disposed in the light path of the V-LED 20a and reflects the part of the V-light, which is emitted from the V-LED 20a, into the V-light quantity detector 302a and passes the rest of the V-light to the combiner 23. In a like manner, a mirror 303b, a mirror 303c, and a mirror 303d are disposed in the light paths of the B-LED 20b, the G-LED 20c, and the R-LED 20d, respectively. The mirror 303b reflects a part of the B-light, which is emitted from the B-LED 20b, into the B-light quantity detector 302b and passes the rest of the B-light to the combiner 23. The mirror 303c reflects a part of the G-light, which is emitted from the G-LED 20c, into the G-light quantity detector 302b and passes the rest of the G-light to the combiner 23. The mirror 303d reflects a part of the R-light, which is emitted from the R-LED 20*d*, into the R-light quantity detector 302*b* and passes the rest of the R-light to the combiner 23. The B-light quantity detector 302*b* obtains the part of the B-light through the mirror 303*b* to detect the light quantity of the B-light emitted from B-LED 20*b*. The G-light quantity detector 302*c* obtains the part of the G-light through the mirror 303*c* to detect the light quantity of the G-light emitted from the G-LED 20*c*. The R-light quantity detector 302*d* obtains the part of the R-light through the mirror 303*d* to detect the light quantity of the R-light emitted from the R-LED 20*d*.

Figure 13:
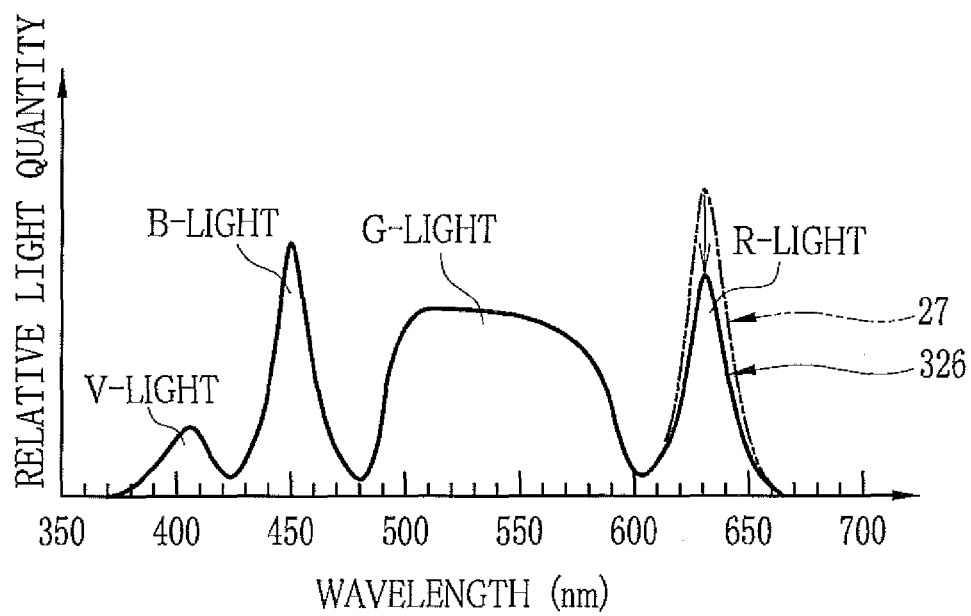
FIG. 13 is a graph illustrating a spectrum of the first multicolor spectrum light in the case where the semiconductor light source is aged with time.
Figure 14:
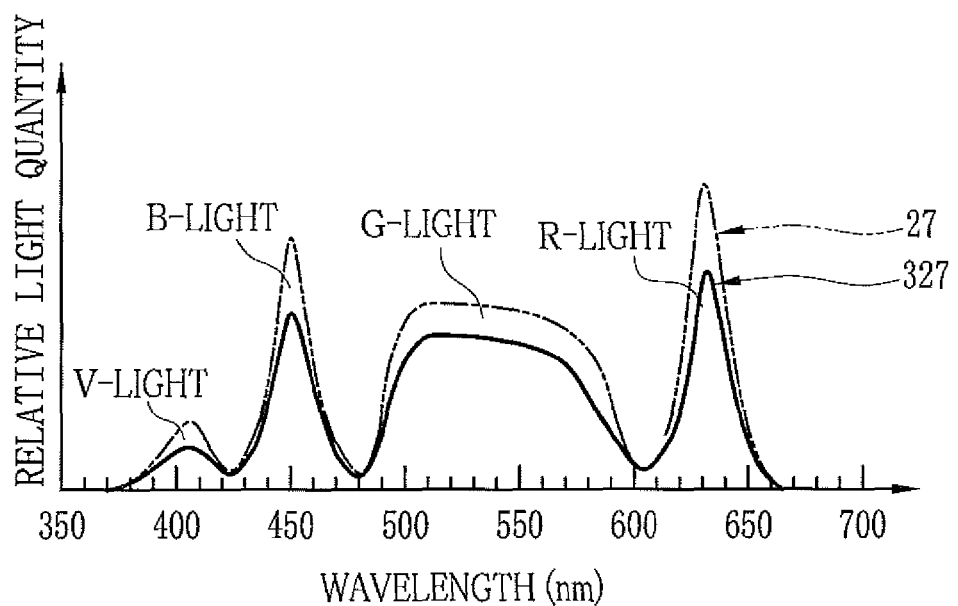
FIG. 14 is a graph illustrating a spectrum of the first multicolor spectrum light with its light quantity adjusted in accordance with the most aged light source.

The light quantity detector 301 inputs the light quantities of the V-light, the B-light, the G-light, and the R-light, which are detected by the respective light quantity detectors 302*a* to 302*d*, to the light source controller 22. In the light source controller 22, the aging detector 304 detects aging of each of the LEDs 20*a* to 20*d* based on the conditions (e.g. the drive currents and the like) for driving the LEDs 20*a* to 20*d* and the light quantities of the light of the respective colors actually detected by the light quantity detector 301. To be more specific, the aging detector 304 detects the most aged light source, in which the light quantity is most reduced relative to the predetermined light quantity, among the LEDs 20*a* to 20*d*. Based on the light quantity of the most aged light source detected by the aging detector 304, the light source controller 22 sets the light quantities of the rest of the light sources. For example, as illustrated in FIG. 13, suppose the light source controller 22 drives the LEDs 20*a* to 20*d* in accordance with the specified conditions for emitting the first multicolor spectrum light 27, but the light actually emitted is multicolor spectrum light 326, in which the light quantity of the R-light is less than the specified light quantity necessary to emit the first multicolor spectrum light 27, due to aging of the R-LED 20*d*. In the first multicolor spectrum light 326, the light quantities of the V-light, the B-light, and the G-light meet the specified values. In this case, the aging detector 304 detects the R-LED 20*d* as the most aged light source. As illustrated in FIG. 14, the light source controller 22 reduces the light quantities of the V-light, the B-light, and the G-light in accordance with the light quantity of the R-light emitted from the R-LED 20*d*. Thereby the light source controller 22 allows the emission of adjusted first multicolor spectrum light 327, in which the balance among the light quantity of the R-light emitted from the aged R-LED 20*d* and the light quantities of the V-light, the B-light, and the G-light is restored. In other words, in the case where shortage of light quantity is detected in at least one of the LEDs 20*a* to 20*d*, the light source controller 22 sets the light quantities of the rest of the light sources based on the light quantity of the most aged light source with the largest shortage of the light quantity relative to the specified light quantity of the corresponding LED. Thereby the first multicolor spectrum light 327, in which the balance among the light of each color is restored, is emitted.

As described above, the light quantity of the light from each of the LEDs 20*a* to 20*d* is detected. Based on the light quantity of the light source most aged among the LEDs 20*a* to 20*d*, the light quantities of the rest of the LEDs are set. Thus, the light source controller 22 allows the light source unit 20 to stably emit the first multicolor spectrum light 27 or the second multicolor spectrum light 201, in which the balance among the light of each color is restored. As described above, the first multicolor spectrum light 27 or 327 or the second multicolor spectrum light 201, in which the balance among the light of each color is restored, is emitted stably. This eliminates the need for calculating, re-calculating, and preparing parameters (e.g. a matrix used in matrix processing) for signal processing and image processing for generating an endoscopic image. In a case where color-mixing occurs in a color filter of the image sensor 48, the signal cannot be corrected enough even if the parameters for signal processing and image processing are recalculated or prepared. However, the object is observed constantly and stably according to the embodiments described above.

In the third embodiment, it is preferred that the light quantity detector 301 detects the light quantity of the light of each color at least at the time of calibration. It is particularly preferred that the light quantity detector 301 repeats the detection of the light quantity of the light of each color during the emissions of the LEDs 20*a* to 20*d* for the observation of the object and provides the feedback to the light source controller 22, to adjust the distribution (balance) in the first multicolor spectrum light 27 (or the like) real time.

Fourth Embodiment

Figure 15:
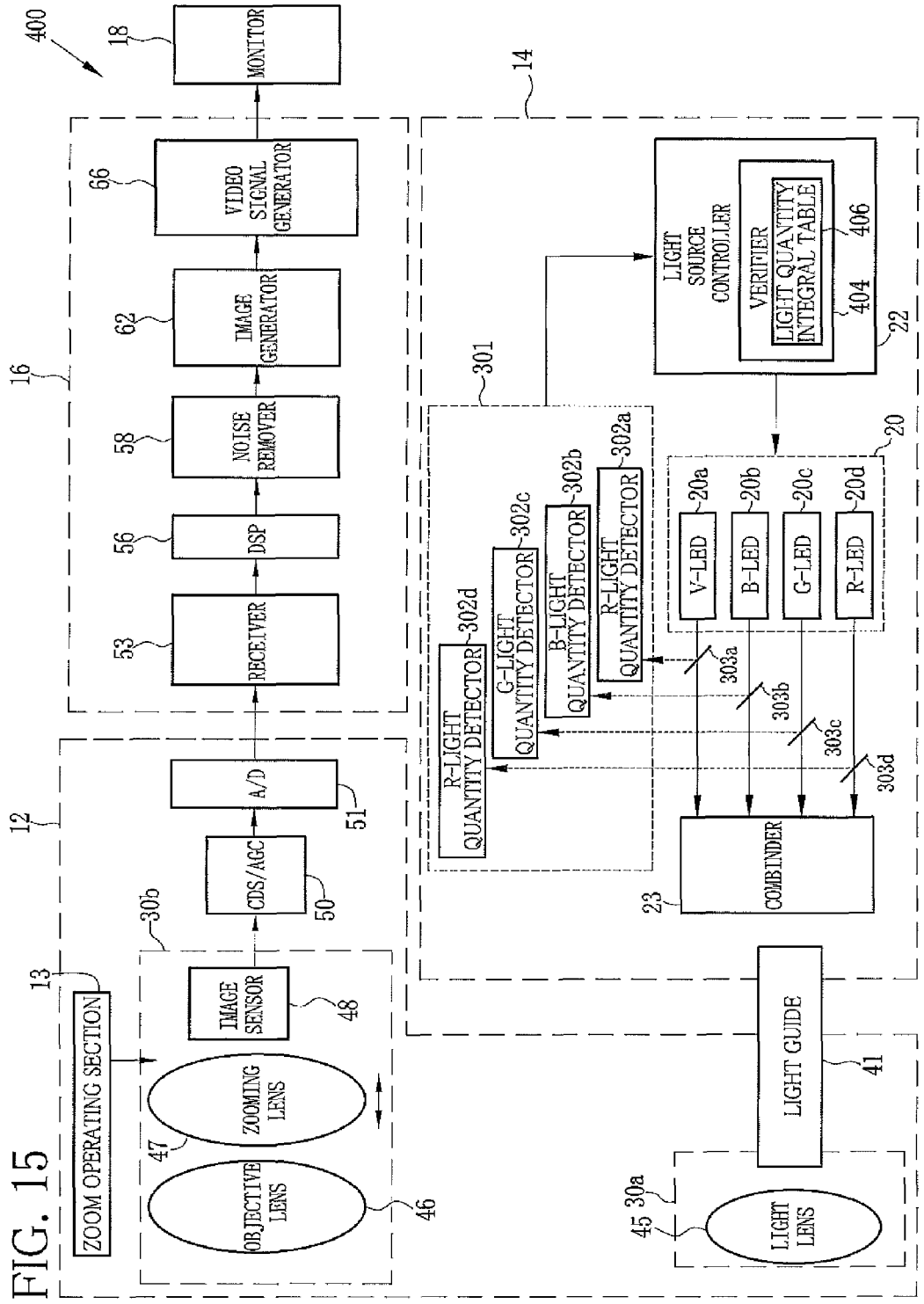
FIG. 15 is a block diagram illustrating an endoscope system with a verifier.

The aging of the LEDs 20*a* to 20*d* is detected in the endoscope system 300 in the third embodiment. There may be cases where the first multicolor spectrum light 27 cannot not be generated or emitted properly or accurately due to a reason other than the aging of the LEDs 20*a* to 20*d*. In this case, an endoscope system 400 illustrated in FIG. 15 is provided with the light quantity detector 301 similar to that provided in the endoscope system 300 of the third embodiment. The light source controller 22 is provided with a verifier 404 instead of the aging detector 304.

The verifier 404 previously stores the light quantity integral $S1_X$ of the continuous-spectrum light 26 of the xenon lamp in the first wavelength band, the light quantity integral $S2_X$ of the continuous-spectrum light 26 in the second wavelength band, and the light quantity integral $S3_X$ of the continuous-spectrum light 26 in the third wavelength band in a light quantity integral table 406. Here, the continuous-spectrum light 26 is to be emulated.

Based on the light quantity integral table 406 and the result of the detection performed by the light quantity detector 301, the verifier 404 verifies whether the actually-emitted multicolor spectrum light corresponds to or is the first multicolor spectrum light 27. To be more specific, based on the actual light quantities of the respective LEDs 20*a* to 20*d*, which are detected by the light quantity detector 301, the verifier 404 calculates the light quantity integral $S1_E$ of the actually-emitted multicolor spectrum light in the first wavelength band and compares the light quantity integral $S1_E$ with the light quantity integral $S1_X$ of the continuous-spectrum light 26 in the first wavelength band stored in the light quantity integral table 406. In a like manner, the verifier 404 calculates the light quantity integral $S2_E$ of the actually-emitted multicolor spectrum light in the second wavelength band and compares the light quantity integral $S2_E$ with the light quantity integral $S2_X$ of the continuous-spectrum light 26 in the second wavelength band stored in the light quantity integral table 406. The verifier 404 calculates the light quantity integral $S3_E$ of the actually-emitted multicolor spectrum light in the third wavelength band and compares the light quantity integral $S3_X$ of the continuous-spectrum light 26 in the third wavelength band stored in the light quantity integral table 406.

Based on the comparisons, the verifier 404 determines that the first multicolor spectrum light 27 is emitted properly (in other words, the actually-emitted multicolor spectrum light is the first multicolor spectrum light 27) in the case where each of an error in the light quantity integral $S1_E$ relative to the light quantity integral $S1_X$ of the continuous-spectrum light 26, an error in the light quantity integral $S2_E$ relative to the light quantity integral $S2_X$, and an error in the light quantity integral $S3_E$ relative to the light quantity integral $S3_X$ falls within the tolerance (for example, the tolerance in the order of less than or equal to 10%). In this case, the light source controller 22 continues the emission of the first multicolor spectrum light 27.

On the other hand, the verifier 404 determines that the first multicolor spectrum light 27 is not emitted properly in the case where at least one of the error in the light quantity integral $S1_E$ relative to the light quantity integral $S1_X$ of the continuous-spectrum light 26, the error in the light quantity integral $S2_E$ relative to the light quantity integral $S2_X$, and the error in the light quantity integral $S3_E$ relative to the light quantity integral $S3_X$ exceeds the tolerance. In this case, the light source controller 22 performs the feedback control of the LEDs 20a to 20d based on the result of the verification performed by the verifier 404. In other words, the light source controller 22 controls the LEDs 20a to 20d to adjust their light quantities based on the errors (the error in the light quantity integral $S1_E$ relative to the light quantity integral $S1_X$ of the continuous-spectrum light 26, the error in the light quantity integral $S2_E$ relative to the light quantity integral $S2_X$, and the error in the light quantity integral $S3_E$ relative to the light quantity integral $S3_X$) calculated by the verifier 404. Thereby the illumination light is adjusted into the first multicolor spectrum light 27 constantly and properly.

In the endoscope system 400 of the fourth embodiment, the verifier 404 calculates or obtains the error in the light quantity integral $S1_E$ relative to the light quantity integral $S1_X$ of the continuous-spectrum light 26, the error in the light quantity integral $S2_E$ relative to the light quantity integral $S2_X$, and the error in the light quantity integral $S3_E$ relative to the light quantity integral $S3_X$ and determines or verifies whether the first multicolor spectrum light 27 is emitted properly based on the errors obtained. Instead, the verifier 404 may use only the error in the light quantity integral $S1_E$ relative to the light quantity integral $S1_X$ and the error in the light quantity integral $S2_E$ relative to the light quantity integral $S2_X$, to determine or verify whether the first multicolor spectrum light 27 is emitted properly. In this case, the error in the light quantity integral $S3_E$ relative to the light quantity integral $S3_X$ is not used for the verification.

The endoscope system 400 according to the fourth embodiment uses the light quantity detector 301 to detect the light quantities of the respective LEDs 20a to 20d. Instead of the light quantities of the LEDs 20a to 20d, the light quantity detector 301 may detect the spectrum of the light from each of the LEDs 20a to 20d. Also in this case, whether the first multicolor spectrum light 27 is emitted properly is verified in a manner similar to the fourth embodiment.

Figure 16:
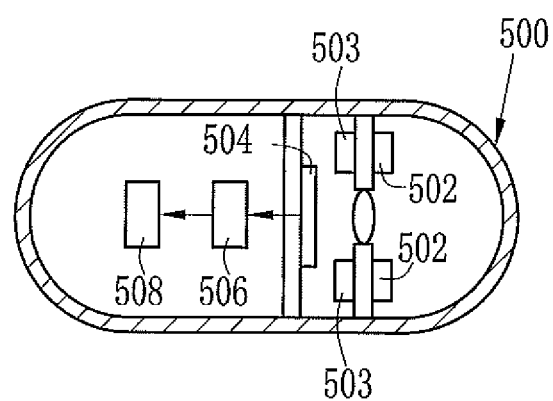
FIG. 16 is a schematic view of a capsule endoscope system.

In the above embodiments and the modified examples, the present invention is implemented by using the endoscope system having the endoscope 12 provided with the image sensor 48 and inserted into the body cavity. The aspects of the present invention are suitable for a capsule endoscope system. For example, as illustrated in FIG. 16, a capsule endoscope system at least comprises a capsule endoscope 500 and a processor device (not shown).

The capsule endoscope 500 comprises light source units 502, light source controllers 503, an image sensor 504, an image generator 506, and a transmission/reception antenna 508. The light source unit 502 comprises a V-LED, a B-LED, a G-LED, and an R-LED, in a manner similar to the light source unit 20. The V-LED emits violet light V. The B-LED emits blue light B. The G-LED emits green light G. The R-LED emits red light R.

The light source controller 503 controls the light source unit 502 in a manner similar to the light source controller 22 described in the above embodiments and the modified examples. The light source controller 503 is wirelessly communicable with the processor device of the capsule endoscope system through the transmission/reception antenna 508. The processor device of the capsule endoscope system is substantially similar to the processor device 16 described in the above embodiments and the modified examples except that the image generator 506 is provided in the capsule endoscope 500 and the generated endoscopic images are transmitted through the transmission/reception antenna 508 to the processor device. The image sensor 504 is similar to the image sensor 48 described in the above embodiments and the modified examples.

Note that, in the above embodiments and the modified examples, the light source controller 22 allows generating the first multicolor spectrum light 27 emulating the white light of the xenon lamp. Instead, the light source controller 22 may allow generating the first multicolor spectrum light 27 emulating the continuous-spectrum light other than the white light of the xenon lamp. For example, a halogen lamp may be used instead of the xenon lamp in a conventional endoscope system. The light source controller 22 may allow generating the first multicolor spectrum light 27 emulating the light of the halogen lamp. A doctor or a like may choose the type of the light (or the type of the lamp) to be emulated. In a like manner, light of a broadband light source comprising an excitation light source for emitting excitation light and phosphor, which emits fluorescence by the application of the excitation light, may be emulated. The continuous-spectrum light emitted from a broadband light source comprising a semiconductor light source may be emulated. The broadband light source may be a combination of, for example, an excitation light source that emits UV-light, violet light, or blue light with phosphor that emits fluorescence from green to yellow (or red) by the application of the UV-light, the violet light, or the blue light. The broadband light source comprising the semiconductor light source is, for example, a semiconductor light source that emits the white light. As described above, in the case where the continuous-spectrum light (including pseudo white light, which looks substantially white, and the light other than the white light) other than that of the xenon lamp is to be emulated, the first multicolor spectrum light is generated in a manner similar to that emulating the white light of the xenon lamp.

In the above embodiments and the modified examples, the LEDs of the four colors, the V-LED 20a, the B-LED 20b, the G-LED 20c, and the R-LED 20d are used. The colors (wavelengths) of the light from the light sources used in the light source device 14 may be other than those described above and in the combination other than those described above. Instead of or in addition to the LEDs, other semiconductor light sources, for example, an LD (laser diode) may be used.

In the above embodiments and the modified examples, the first multicolor spectrum light 27 that is adjusted to enable the observation of the object in a manner comparable to the observation using the continuous-spectrum light 26 of the xenon lamp is applied to the object. In other words, the first multicolor spectrum light 27 that is the illumination light to be applied to the object emulates the continuous-spectrum light 26 from the xenon lamp. Instead, the light reflected from the object and incident on the image sensor 48 may emulate the reflection light of the continuous-spectrum light 26 of the xenon lamp. In the case where the light reflected from the object and incident on the image sensor 48 emulates the reflection light of the continuous-spectrum light 26 of the xenon lamp, the signals obtained from the image sensor 48 are similar to those of the case where the illumination light (the first multicolor spectrum light 27) to be applied to the object emulates the continuous-spectrum light 26 from the xenon lamp.

For example, in the case where the first multicolor spectrum light 27 is applied to the object, the light source controller 22 controls the light quantities of the LEDs 20a to 20d such that the light quantity integral of the light in the first wavelength band incident on the image sensor 48 equals the light quantity integral of the reflection light in the first wavelength band reflected from the object irradiated with the continuous-spectrum light 26 of the xenon lamp and the light quantity integral of the light in the second wavelength band incident on the image sensor 48 equals the light quantity integral of the reflection light in the second wavelength band reflected from the object irradiated with the continuous-spectrum light 26 of the xenon lamp. Thereby, the light reflected from the object irradiated with the first multicolor spectrum light 27 and incident on the image sensor 48 emulates the continuous-spectrum light 26 of the xenon lamp. As a result, the object irradiated with the first multicolor spectrum light 27 is able to be compared with (or observed in a manner similar to) the object irradiated with the continuous-spectrum light 26 of the xenon lamp.

The light quantities of the LEDs 20a to 20d may be controlled by taking the properties of the color filters of the respective colors, which are provided to the pixels in the image sensor 48, into consideration. To be more specific, the light source controller 22 makes a signal obtained from a first color pixel (for example, a B-pixel) provided with a first color filter (for example a B-color filter) in the case where the object is irradiated with the first multicolor spectrum light 27 equal to a signal obtained from the first color pixel in the case where the object is irradiated with the continuous-spectrum light 26 of the xenon lamp and makes a signal obtained from a second color pixel (for example, a G-pixel) provided with a second color filter (for example, a G-color filter) in the case where the object is irradiated with the first multicolor spectrum light 27 equal to a signal obtained from the second color pixel in the case where the object is irradiated with the continuous-spectrum light 26 of the xenon lamp. In other words, the first wavelength band, the second wavelength band, and the third wavelength band of the above embodiments are set to the respective wavelength bands corresponding to the RGB color sensor of the image sensor 48.

Thereby the signal obtained from the first color pixel corresponds to the light quantity integral of the light in the first wavelength band. The signal obtained from the second color pixel is the light quantity integral of the light in the second wavelength band. The signal obtained from the third color pixel is the light quantity integral of the light in the third wavelength band. Hence the signal obtained from the first color pixel is referred to as the light quantity integral obtained from the first color pixel. The signal obtained from the second color pixel is referred to as the light quantity integral obtained from the second color pixel. The signal obtained from the third color pixel is referred to as the light quantity integral obtained from the third color pixel. The light quantity integral obtained from each pixel is a value determined by exposure time of the pixel (in other words, a value integrated over time), but has substantially the same function as (corresponds to) the light quantity integral described in the above embodiments and the modified examples. In the case where the exposure times of the first, second and third color pixels are different from one another, the light quantity integral obtained from each pixel is adjusted by taking the exposure time of the pixel into consideration.

Various changes and modifications are possible in the present invention and may be understood to be within the present invention.

(Additional Item)

An endoscope comprising:

a light source unit having two or more light sources independently emitting light of different colors, the light of the different colors being combined into first multicolor spectrum light having a first multicolor spectrum, the light source unit emitting the first multicolor spectrum light;

an image sensor having a first color pixel and a second color pixel, the first color pixel being provided with a first color filter, the second color pixel being provided with a second color filter, the second color filter being different from the first color filter, the image sensor configured to image an object of interest irradiated with the first multicolor spectrum light; and a light source controller configured to control the light sources, the light source controller making a light quantity integral obtained from the first color pixel of the image sensor in the case where the object is irradiated with the first multicolor spectrum light equal to a light quantity integral obtained from the first color pixel of the image sensor in the case where the object is irradiated with continuous-spectrum light and making a light quantity integral obtained from the second color pixel of the image sensor in the case where the object is irradiated with the first multicolor spectrum light equal to a light quantity integral obtained from the second color pixel of the image sensor in the case where the object is irradiated with the continuous-spectrum light.

What is claimed is:

1. A light source device for an endoscope comprising:
a light source unit having two or more light sources, the light sources independently emitting light of different colors, the light from the light sources being combined into first multicolor spectrum light having a first multicolor spectrum, the light source unit emitting the first multicolor spectrum light; and
a light source controller configured to control the light sources, the light source controller making a light quantity integral of the first multicolor spectrum light in a first wavelength band equal to a light quantity integral of continuous-spectrum light in the first wavelength band and making a light quantity integral of the first multicolor spectrum light in a second wavelength band equal to a light quantity integral of the continuous-spectrum light in the second wavelength band, the continuous-spectrum light including at least a part of a wavelength band of light emitted from a white light source, the second wavelength band being different from the first wavelength band.

2. The light source device according to claim 1, wherein the continuous-spectrum light is white light.

3. The light source device according to claim 2, wherein the white light is emitted from a xenon lamp.

4. The light source device according to claim 1, wherein the first wavelength band is a wavelength range including a violet wavelength range and a blue wavelength range, and the second wavelength band is a green wavelength range.

5. The light source device according to claim 1, wherein the light sources include a violet light source emitting violet light and a blue light source emitting blue light, and the first wavelength band of the first multicolor spectrum light is a wavelength range including the violet light and the blue light.

6. The light source device according to claim 1, wherein the light source controller further makes a light quantity integral of the first multicolor spectrum light in a third wavelength band equal to a light quantity integral of the continuous-spectrum light in the third wavelength band, the third wavelength band being different from each of the first wavelength band and the second wavelength band.

7. The light source device according to claim 6, wherein the third wavelength band is a red wavelength range.

8. The light source device according to claim 1, wherein the light source unit emits second multicolor spectrum light having a second multicolor spectrum through the light sources, the second multicolor spectrum being different from the first multicolor spectrum of the first multicolor spectrum light and different from a spectrum of the continuous-spectrum light, and the light source controller makes a light quantity integral of the second multicolor spectrum light in the first wavelength band greater than the light quantity integral of the continuous-spectrum light in the first wavelength band and makes a light quantity integral of the second multicolor spectrum light in the second wavelength band equal to the light quantity integral of the continuous-spectrum light in the second wavelength band.

9. The light source device according to claim 1, further comprising a light quantity detector for detecting a light quantity of the light from each of the light sources;

wherein the light source controller uses a result of the detection detected by the light quantity detector to set light quantities of the rest of the light sources based on a light quantity of the light source with the largest shortage of the light quantity among the light sources relative to a specified light quantity to generate the first multicolor spectrum light.

10. The light source device according to claim 9, wherein the light quantity detector repeats the detection of the light quantity of the light from each of the light sources while the light sources emit the light.

11. The light source device according to claim 1, further comprising a verifier, the verifier verifying whether the light quantity integral of the first multicolor spectrum light in the first wavelength band equals the light quantity integral of the continuous-spectrum light in the first wavelength band and whether the light quantity integral of the first multicolor spectrum light in the second wavelength band equals the light quantity integral of the continuous-spectrum light in the second wavelength band.

12. The light source device according to claim 11, wherein the light source controller uses a result of the verification verified by the verifier, to control the light sources.

13. An endoscope system comprising:

a light source unit having two or more light sources, the light sources independently emitting light of different colors, the light from the light sources being combined into first multicolor spectrum light having a first multicolor spectrum, the light source unit emitting the first multicolor spectrum light; and a light source controller configured to control the light sources, the light source controller making a light quantity integral of the first multicolor spectrum light in a first wavelength band equal to a light quantity integral of continuous-spectrum light in the first wavelength band and making a light quantity integral of the first multicolor spectrum light in a second wavelength band equal to a light quantity integral of the continuous-spectrum light in the second wavelength band, the continuous-spectrum light including at least a part of a wavelength band of light emitted from a white light source, the second wavelength band being different from the first wavelength band.

14. The endoscope system according to claim 13, wherein the light source unit emits second multicolor spectrum light having a second multicolor spectrum through the light sources, the second multicolor spectrum being different from the first multicolor spectrum of the first multicolor spectrum light and different from a spectrum of the continuous-spectrum light, and the light source controller makes a light quantity integral of the second multicolor spectrum light in the first wavelength band greater than the light quantity integral of the continuous-spectrum light in the first wavelength band and makes a light quantity integral of the second multicolor spectrum light in the second wavelength band equal to the light quantity integral of the continuous-spectrum light in the second wavelength band.

15. The endoscope system according to claim 14, further comprising a model detector, the model detector detecting a model of an endoscope connected and inputting a result of the detection to the light source controller, wherein the light source controller switches the light emitted from the light source unit between the first multicolor spectrum light and the second multicolor spectrum light in accordance with the model of the endoscope detected by the model detector.

16. The endoscope system according to claim 15, wherein the light source controller allows the light source unit to emit the first multicolor spectrum light in a case where the endoscope is of a model using the continuous-spectrum light and allows the light source unit to emit the second multicolor spectrum light in a case where the endoscope is of a model not using the continuous-spectrum light.

17. A method for operating a light source device for an endoscope, the light source device comprising a light source unit having two or more light sources, the light sources independently emitting light of different colors, the light from the light sources being combined into first multicolor spectrum light having a first multicolor spectrum, the light source unit emitting the first multicolor spectrum light, the method comprising the steps of:

preparing the light source device; and controlling the light sources with a light source controller, the light source controller making a light quantity integral of the first multicolor spectrum light in a first wavelength band equal to a light quantity integral of continuous-spectrum light in the first wavelength band and making a light quantity integral of the first multicolor spectrum light in a second wavelength band equal to a light quantity integral of the continuous-spectrum light in the second wavelength band, the continuous-spectrum light including at least a part of a wavelength band of light emitted from a white light source, the second wavelength band being different from the first wavelength band.

* * * * *